(12) United States Patent
Kung et al.

(10) Patent No.: US 8,791,279 B2
(45) Date of Patent: Jul. 29, 2014

(54) PROCESS FOR PREPARING TAXOIDS FROM BACCATIN DERIVATIVES USING LEWIS ACID CATALYST

(75) Inventors: Liang-Rern Kung, Taichung (TW);
Shih-Sheng Chang, Taichung (TW);
Tung-Shen Fang, Taichung (TW);
Shu-Fen Lin, Changhua County (TW);
Cheng-Chang Chang, Taichung (TW);
Chia-Hui Chen, Miaoli County (TW);
Yi-Ting Hung, Tainan (TW);
Ming-Ching Cheng, Taichung (TW)

(73) Assignee: Yung Shin Pharm. Ind. Co., Ltd., Tachia Taichung (TW)

( * ) Notice: Subject to any disclaimer, the term of this patent is extended or adjusted under 35 U.S.C. 154(b) by 266 days.

(21) Appl. No.: 13/239,205

(22) Filed: Sep. 21, 2011

(65) Prior Publication Data

US 2012/0149925 A1 Jun. 14, 2012

Related U.S. Application Data

(60) Provisional application No. 61/422,472, filed on Dec. 13, 2010.

(51) Int. Cl.
*C07D 305/00* (2006.01)
*C07D 305/06* (2006.01)
*C07D 305/14* (2006.01)

(52) U.S. Cl.
CPC ............ *C07D 305/14* (2013.01); *C07D 305/06* (2013.01)
USPC ......................................... 549/510; 549/511

(58) Field of Classification Search
CPC .................................................... C07D 305/14
USPC .................................................. 549/510, 511
See application file for complete search history.

(56) References Cited

U.S. PATENT DOCUMENTS 5,466,834 A * 11/1995 Holton ........................... 549/510
5,773,461 A * 6/1998 Wittman et al. ............... 514/449

(Continued)

FOREIGN PATENT DOCUMENTS

EP 01400971 A2 12/1990

OTHER PUBLICATIONS

Amancha, et al.; "Diels-Alder Reactions of Acyclic α-Cyano α, β-Alkenones: a New Approach to Highly Substituted Cyclohexene System"; Tetrahedron; vol. 66, pp. 871-877 (2010).

(Continued)

*Primary Examiner* — Andrew D Kosar
*Assistant Examiner* — Raymond Covington
(74) *Attorney, Agent, or Firm* — Perkins Coie LLP; Viola T. Kung

(57) ABSTRACT

The present invention relates to a process of preparing a taxoid (X) by reacting a protected baccatin derivative (B) with a β-lactam (C) in the presence of one or more Lewis acids and a base agent. The present invention also relates to a process of preparing the protected baccatin derivative (B) from a baccatin derivative (A) comprising a protection reaction catalyzed by one or more Lewis acids with an optional base agent.

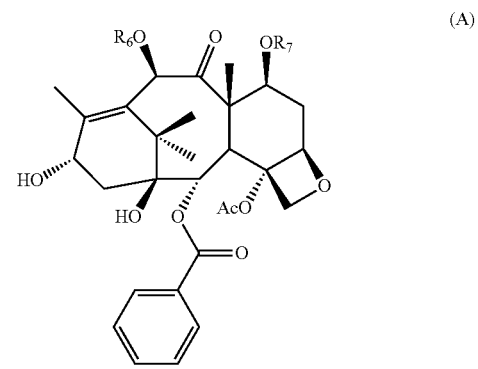

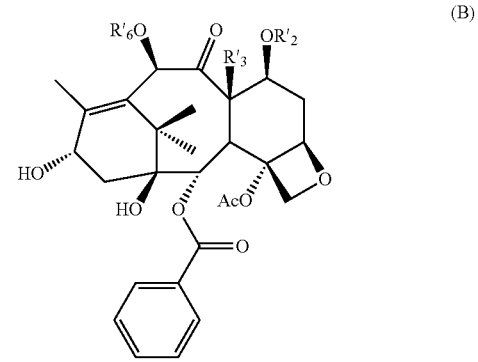

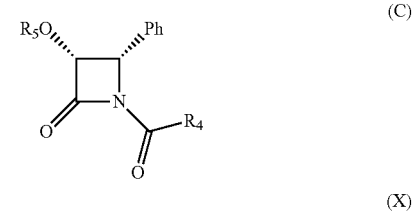

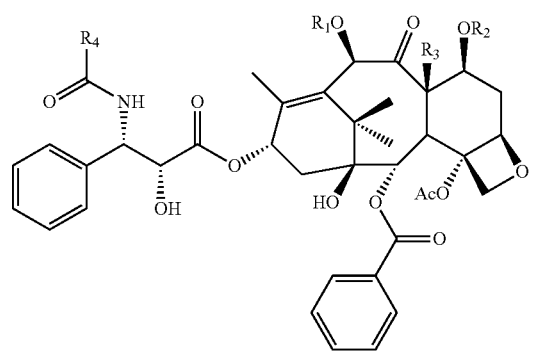

23 Claims, No Drawings

(56) References Cited

U.S. PATENT DOCUMENTS

| | | | |
|---|---|---|---|
| 5,840,929 A * | 11/1998 | Chen | 549/510 |
| 5,874,595 A | 2/1999 | Damen et al. | |
| 5,962,705 A | 10/1999 | Didier et al. | |
| 6,911,549 B1 * | 6/2005 | Hester et al. | 549/510 |

OTHER PUBLICATIONS

Bouchard, et al.; "Improved Access to 19-Nor-7β,8β-Methylene-Taxoids and Formation of a 7-Membered C-Ring Analog of Docetaxel by Electrochemistry"; Tetrahedron Letters; vol. 5, No. 52, pp. 9713-9716 (1994).

Chen, et al.; "On the Reaction of Taxol With Dast"; Tetrahedron Letters; vol. 35, No. 1, pp. 41-44 (1994).

Denis, et al.; "A Highly Efficient, Practical Approach to Natural Taxol"; J. Am. Chem. Soc.; vol. 110, pp. 5917-5919 (1988).

Holton, et al.; "Selective Protection of the C(7) and C(10) Hydroxyl Groups in 10-Deacetyl Baccatin III"; Tetrahedron Letters; vol. 39, pp. 2883-2886 (1998).

Johnson, et al.; "Efficient Method for the t-Butyldimethylsilylation of Alcohols with N, O-Bis (t-butyldimethylsilyl)acetamide"; Tetrahedron Letters; vol. 37, No. 5, pp. 605-608 (1996).

Liu, et al.; "Lithium Naphthalenide Induced Reductive Alkylation of α-Cyano Ketones. A General Method for Regiocontrol of α, α-Dialkylation of Ketones"; Tetrahedron Letters; vol. 39, pp. 4183-4186 (1998).

Morihira, et al.; "Enantioselective Total Synthesis of Taxol"; J. Am. Chem. Soc.; vol. 120, pp. 12980-12981 (1998).

Nicolaou, et al.; "Synthesis of Novel Taxoids"; J. Am. Chem. Soc.; vol. 116, pp. 1591-1592 (1994).

Nicolaou, et al.; "Total Synthesis of Taxol. 1. Retrosynthesis, Degradation, and Reconstitution"; J. Am. Chem. Soc.; vol. 117, pp. 624-633 (117), (1995).

Samaranayake, et al.; "Modified Taxols. $5._1$ Reaction of Taxol with Electrophilic Reagents and Preparation of a Rearranged Taxol Derivative with Tubulin Assembly Activity"; J. Org. Chem.; vol. 56, pp. 5114-5119 (1991).

Wozniak, et al.; "Stereodefined Dinucleoside (3',5')-propionamidophosphonates and β-cyanoethylphosphonates and their incorporation into modified oligonucleotides"; Tetrahedron Letters; vol. 50, pp. 2620-2623 (2009).

* cited by examiner

PROCESS FOR PREPARING TAXOIDS FROM BACCATIN DERIVATIVES USING LEWIS ACID CATALYST

CROSS-REFERENCE TO RELATED APPLICATIONS

The present application claims priority to U.S. Provisional Application No. 61/422,472 filed on Dec. 13, 2010, which is incorporated herein by reference in its entirety.

FIELD OF THE INVENTION

The present disclosure relates to a process of preparing taxoids from baccatin derivatives using one or more Lewis acids as catalysts.

BACKGROUND OF THE INVENTION

Taxoids are compounds derived from taxol (also referred to as paclitaxel), an isolated natural product and an important anticancer drug. It stabilizes microtubules during mitosis to treat patients with different kinds of cancer (e.g. ovarian cancer, breast cancer and lung cancer). Natural taxol has been isolated from the stem bark of Yew. However, the extraction and purification of taxol from Yew are expensive.

Instead of obtaining taxol from Yew, semi-synthesis of taxol from a baccatin derivative (e.g. suitable protected 10-deacetylbaccatin III (10-DAB)) is a more economic way.

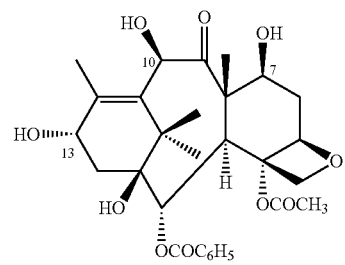

10-Deacetylbaccatin III (10-DAB)

Preliminary studies by Potier's group (*P.C.R. Acad. Sci. Paris II*, 299, 1039, 1984; *Tetrahedron* 42, 4451, 1986) showed that the hydroxyl groups of 10-DAB have different reactivities toward acetic anhydride in pyridine. The relative reactivity was C(7)-OH>C(10)-OH>C(13)-OH>C(1)-OH. In 1988, Greene's group (*J. Am. Chem. Soc.*, 110, 5917, 1988) reported the selective silylation of the C(7) hydroxyl group with triethylsilyl chloride in pyridine to produce 7-TES-10-DAB in 85% yield. The protected 10-DAB derivatives prepared by Potier's and Greene's group are important precursors to taxol synthesis. After a decade, Holton's group (*Tetrahedron Lett.*, 39, 2883, 1998) provided new methods for the selective acylation and silylation of C(10)-OH of 10-DAB and for the selective silylation of C(7)-OH of 10-DAB. U.S. Pat. No. 5,962,705 (Didier et al) discloses that C(7)-OH and C(10)-OH could be methylated simultaneously to obtained 7,10-dimethoxy-10-DAB. U.S. Pat. No. 5,874,595 discloses a method for preparing baccatin III directed from 10-deacetylbaccatin III comprising: acetylating 10-deacetylbaccatin III with acetic anhydride, a mixed anhydride of acetic acid and any other carboxylic acid or an acetyl halide, and a Lewis acid catalyst.

There is a need for a regioselective method that is applicable to synthesize various taxoids (e.g. paclitaxel, docetaxel, larotaxel, cabazitaxel, and derivatives thereof).

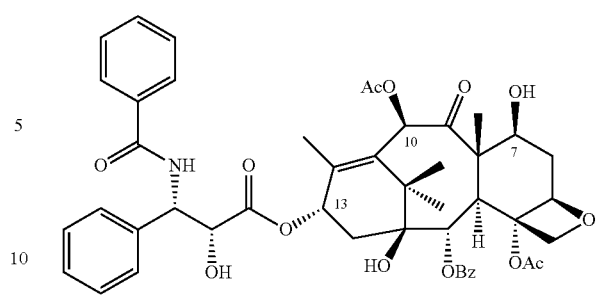

Paclitaxel (Taxol)

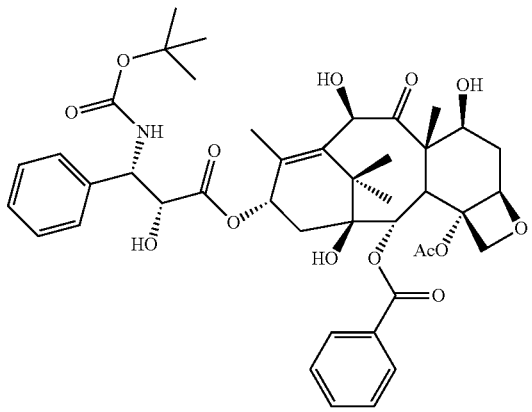

Docetaxel

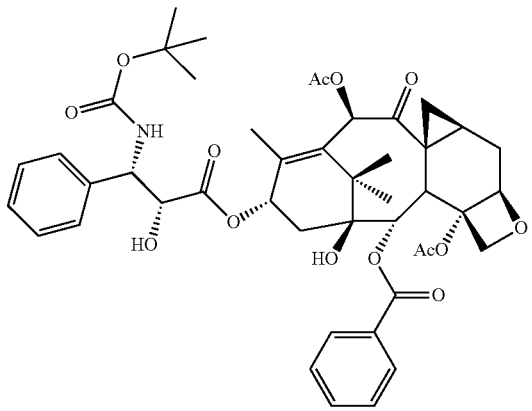

Larotaxel

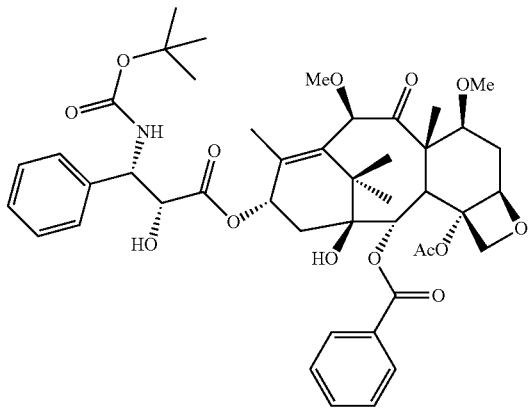

Cabazitaxel

BRIEF SUMMARY OF THE INVENTION

The present invention relates to a process of preparing a taxoid (X) by reacting a protected baccatin derivative (B) with a β-lactam (C) in the presence of one or more Lewis acids and a base agent. The present invention also relates to a process of preparing the protected baccatin derivative (B) from a baccatin derivative (A) comprising a protection reaction catalyzed by one or more Lewis acids with an optional base agent.

DETAILED DESCRIPTION OF THE INVENTION

As used herein, unless otherwise specified, "Ac" means acetyl; "Ph" means phenyl; "Bz" means benzoyl; "TES" means triethylsilyl; "10-DAB" means 10-deacetylbaccatin III; "DMAP" means N,N-dimethyl-4-amino-pyridine; "Tf" means triflyl ($CF_3SO_2$—); and "DCM" means dichloromethane.

When present, unless otherwise specified, the following terms are generally defined as, but are not limited to, the following:

Halo substituents are taken from fluorine, chlorine, bromine, and iodine.

"Alkyl" refers to groups of from 1 to 12 carbon atoms inclusively, either straight chained or branched, more preferably from 1 to 8 carbon atoms inclusively, and most preferably 1 to 6 or 1 to 4 carbon atoms inclusively.

"Alkenyl" refers to groups of from 2 to 12 carbon atoms inclusively, either straight or branched containing at least one double bond but optionally containing more than one double bond.

"Alkynyl" refers to groups of from 2 to 12 carbon atoms inclusively, either straight or branched containing at least one triple bond but optionally containing more than one triple bond, and additionally optionally containing one or more double bonded moieties.

"Alkoxy" refers to the group alkyl-O— wherein the alkyl group is as defined above including optionally substituted alkyl groups as also defined above.

"Aryl" refers to an unsaturated aromatic carbocyclic group of from 6 to 14 carbon atoms inclusively having a single ring (e.g., phenyl) or multiple condensed rings (e.g., naphthyl or anthryl). Preferred aryls include phenyl, naphthyl and the like.

"Arylalkyl" refers to aryl-alkyl-groups preferably having from 1 to 6 carbon atoms inclusively in the alkyl moiety and from 6 to 10 carbon atoms inclusively in the aryl moiety. Such arylalkyl groups are exemplified by benzyl, phenethyl and the like.

"Arylalkenyl" refers to aryl-alkenyl-groups preferably having from 2 to 6 carbon atoms in the alkenyl moiety and from 6 to 10 carbon atoms inclusively in the aryl moiety.

"Arylalkynyl" refers to aryl-alkynyl-groups preferably having from 2 to 6 carbon atoms inclusively in the alkynyl moiety and from 6 to 10 carbon atoms inclusively in the aryl moiety.

"Cycloalkyl" refers to cyclic alkyl groups of from 3 to 12 carbon atoms inclusively having a single cyclic ring or multiple condensed rings which can be optionally substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, or multiple ring structures such as adamantyl, and the like.

"Heteroaryl" refers to a monovalent aromatic heterocyclic group of from 1 to 10 carbon atoms inclusively and 1 to 4 heteroatoms inclusively selected from oxygen, nitrogen and sulfur within the ring. Such heteroaryl groups can have a single ring (e.g., pyridyl or furyl) or multiple condensed rings (e.g., indolizinyl or benzothienyl).

"Heterocycle" refers to a saturated or unsaturated group having a single ring or multiple condensed rings, from 1 to 8 carbon atoms inclusively and from 1 to 4 hetero atoms inclusively selected from nitrogen, sulfur or oxygen within the ring. Such heterocyclic groups can have a single ring (e.g., piperidinyl or tetrahydrofuryl) or multiple condensed rings (e.g., indolinyl, dihydrobenzofuran or quinuclidinyl). Preferred heterocycles include piperidinyl, pyrrolidinyl and tetrahydrofuryl.

Examples of heterocycles and heteroaryls include, but are not limited to, furan, thiophene, thiazole, oxazole, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, pyrrolidine, indoline and the like.

Unless otherwise specified, positions occupied by hydrogen in the foregoing groups can be further substituted with substituents exemplified by, but not limited to, hydroxy, oxo, nitro, methoxy, ethoxy, alkoxy, substituted alkoxy, trifluoromethoxy, haloalkoxy, fluoro, chloro, bromo, iodo, halo, methyl, ethyl, propyl, butyl, alkyl, alkenyl, alkynyl, substituted alkyl, trifluoromethyl, haloalkyl, hydroxyalkyl, alkoxyalkyl, thio, alkylthio, acyl, carboxy, alkoxycarbonyl, carboxamido, substituted carboxamido, alkylsulfonyl, alkylsulfinyl, alkylsulfonylamino, sulfonamido, substituted sulfonamido, cyano, amino, substituted amino, alkylamino, dialkylamino, aminoalkyl, acylamino, amidino, amidoximo, hydroxamoyl, phenyl, aryl, substituted aryl, aryloxy, arylalkyl, arylalkenyl, arylalkynyl, pyridyl, imidazolyl, heteroaryl, substituted heteroaryl, heteroaryloxy, heteroarylalkyl, heteroarylalkenyl, heteroarylalkynyl, cyclopropyl, cyclobutyl, cyclopentyl, cyclohexyl, cycloalkyl, cycloalkenyl, cycloalkylalkyl, substituted cycloalkyl, cycloalkyloxy, pyrrolidinyl, piperidinyl, morpholino, heterocycle, (heterocycle)oxy, and (heterocycle)alkyl; and preferred heteroatoms are oxygen, nitrogen, and sulfur. It is understood that where open valences exist on these substituents they can be further substituted with alkyl, cycloalkyl, aryl, heteroaryl, and/or heterocycle groups, that where these open valences exist on carbon they can be further substituted by halogen and by oxygen-, nitrogen-, or sulfur-bonded substituents, and where multiple such open valences exist, these groups can be joined to form a ring, either by direct formation of a bond or by formation of bonds to a new heteroatom, preferably oxygen, nitrogen, or sulfur. It is further understood that the above substitutions can be made provided that replacing the hydrogen with the substituent does not introduce unacceptable instability to the molecules of the present invention, and is otherwise chemically reasonable. Preferred substituents are hydroxy, oxo, nitro, methoxy, ethoxy, alkoxy, substituted alkoxy, trifluoromethoxy, fluoro, chloro, bromo, iodo, halo, methyl, ethyl, propyl, butyl, alkyl, substituted alkyl, trifluoromethyl, acyl, carboxy, alkoxycarbonyl, phenyl, aryl, substituted aryl, aryloxy, arylalkyl, cyclopropyl, cyclobutyl, cyclopentyl, cyclohexyl, cycloalkyl, substituted cycloalkyl.

I) A Process for Preparing a Taxoid (X) from a Protected Baccatin Derivative (B)

One aspect of the present disclosure is directed to a process for preparing a taxoid of general formula (X).

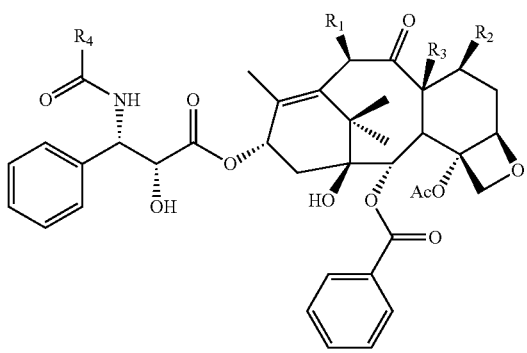

(X)

The process comprises:

a) reacting a protected baccatin derivative of a general formula (B) with a β-lactam of a general formula (C) in the presence of one or more Lewis acids ML and a first base agent to provide a protected taxoid of general formula ($X^0$) having one or more silyl ether protecting groups:

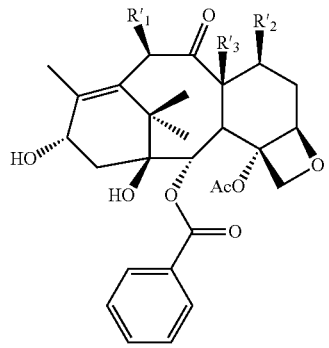

(B)

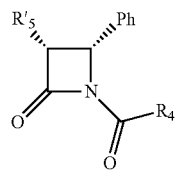

(C)

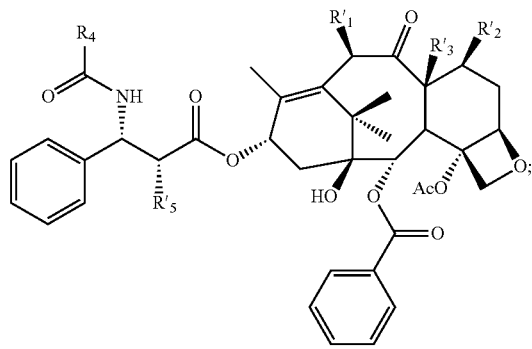

$X^0$ and (b) removing the silyl ether protecting groups to provide the taxoid of general formula (X);

wherein $R'_1$ is alkoxy, aryloxy, —O—C(=O)—$R'_{10}$, or —O—Si($R'_{11}$)($R'_{12}$)($R'_{13}$), preferably alkoxy, —O—C(=O)—$R'_{10}$, or —O—Si($R'_{11}$)($R'_{12}$)($R'_{13}$), and more preferably methoxy, Ac—O—, —O—Si(CH$_3$)$_3$ or —O—Si(CH$_3$CH$_2$)$_3$;

$R'_2$ is alkoxy, aryloxy, —O—C(=O)—$R'_{20}$, or —O—Si($R'_{21}$)($R'_{22}$)($R'_{23}$), or $R'_2$ is H when $R'_3$ is taken together with C7 to form a cycloalkyl ring; preferably $R'_2$ is hydrogen alkoxy, —O—C(=O)—$R'_{20}$, or —O—Si($R'_{21}$)($R'_{22}$)($R'_{23}$), and more preferably is hydrogen, methoxy, —O—Ac, —O—Si(CH$_3$)$_3$ or —O—Si(CH$_3$CH$_2$)$_3$;

$R'_3$ is alkyl, or taken together with C7 to form a cycloalkyl ring, preferably $C_{1-4}$ alkyl (e.g. methyl) or taken together with C7 to form a cycloalkyl ring (e.g. cyclopropyl ring);

$R'_5$ is alkoxy, aryloxy, —O—C(=O)—$R'_{50}$, or —O—Si($R'_{51}$)($R'_{52}$)($R'_{53}$) preferably —O—Si(CH$_2$CH$_3$)$_3$ or —O—Si(CH$_3$)$_3$;

$R_1$ is hydroxyl, alkoxy, aryloxy, or —O—C(=O)—$R_{10}$, preferably hydroxyl, alkoxy (e.g. methoxy), or —O—C(=O)—$R_{10}$ (e.g. —OAc—);

$R_2$ is hydroxyl, hydrogen, alkoxy, alkyl, aryloxy, or —O—C(=O)—$R_{20}$, preferably hydroxyl, hydrogen, or alkoxy (e.g. methoxy);

$R_3$ is alkyl, hydroxyl, alkoxy, aryloxy, or taken together with C7 to form a cycloalkyl ring, preferably alkyl (e.g. methyl) or taken together with C7 to form a cycloalkyl ring (e.g. cyclopropyl ring);

$R_4$ is alkoxy or aryl, preferably —OC(CH$_3$)$_3$, or phenyl; and $R_{10}$, $R_{20}$, $R'_{10}$, $R'_{20}$, and $R'_{50}$, are independently selected from the group consisting of hydrogen, substituted and unsubstituted alkyl, and substituted and unsubstituted aryl; and $R_{11}$, $R_{12}$, $R_{13}$, $R_{21}$, $R_{22}$, $R_{23}$, $R'_{11}$, $R'_{12}$, $R'_{13}$, $R'_{21}$, $R'_{22}$, $R'_{23}$, $R'_{51}$, $R'_{52}$, and $R'_{53}$ are independently selected from the group consisting of hydrogen, substituted and unsubstituted alkyl, substituted and unsubstituted ary.

A Lewis acid is defined by IUPAC as a molecular entity that is an electron-pair acceptor and therefore able to react with a Lewis base to form a Lewis adduct, by sharing the electron pair furnished by the Lewis base. A Lewis acid is defined to be any species that accepts lone pair electrons. A Lewis base is any species that donates lone pair electrons. For example, H$^+$ is a Lewis acid, since it can accept a lone pair, while OH$^-$ and NH$_3$ are Lewis bases, both of which donate a lone pair.

Lewis acids promote carbon-carbon bond formation. Classically, the Friedel-Crafts reaction, the ene reaction, the Diels-Alder reaction, and the Mukaiyama aldol synthesis are catalyzed by ordinary Lewis acids such as AlCl$_3$, TiCl$_4$, BF$_3$.OEt$_2$, or SnCl$_4$.

Lewis acids suitable for the present process have a formula of ML, wherein M is a cation of an element of group IA (alkali), group IIA (alkali earth), group IIIA, group IVA, group IB, group IIB, group IIIB, group IVB, group VB, or group VIIIB (transition metals), or any combination thereof; and L is a counter anion of M. A single Lewis acid or a combination of more than one (e.g. two) different Lewis acids can be used in the present disclosure. A preferred M is a cation of Li, Na, K, Rb, Cs, Be, Mg, Ca, Sr, Ba, Cu, Ag, Au, Zn, Cd, Hg, Fe, Co, Ni, Ru, Rh, Pd, Os, Ir, Pt, Sc, Y, Ti, V, Nb, Co, B, Al, In, Sn, or Ce, or any combination thereof. A more preferred M is a cation of Li, K, Cs, Mg, Sc, Ti, V, Cu, Zn, B, Al, In, Sn, or Ce, or any combination thereof. A preferred L is an anion. Examples of L include, without limitation, oxide (e.g. (OCH(CH$_3$)$_2$)$^-$, and O$^{2-}$), acid radical (e.g. ClO$_4^-$, CO$_3^{2-}$, and triflate (CF$_3$SO$_3^-$)), halide anion (e.g. Br$^-$, Cl$^-$, F$^-$, and I$^-$), and any combination thereof. Examples of preferred Lewis acids ML include, without limitation, LiBr, MgBr$_2$, CsBr, ZnBr$_2$, ZnCl$_2$, CuBr, Cu(CF$_3$SO$_4$)$_2$, BF$_3$.OEt$_2$, KBr, TiCl$_4$, SnCl$_2$, ScCl$_3$, VCl$_3$, AlCl$_3$, InCl$_3$, Al$_2$CO$_3$, CeCl$_3$, Ag$_2$O, ZnClO$_4$, LiClO$_4$, Ti{OCH(CH$_3$)$_2$}$_4$ and any complexes and combination thereof.

Comparing to the reaction carried out without Lewis acid, the presence of Lewis acid provides a more selective reaction, characterized by higher reaction rate, higher yield, more selective product, higher purify of the desired product and less side products. In certain embodiments, the presence of Lewis acid allows the reaction to happen at a less harsh condition, for example, using weaker base, at a lower reaction temperature, etc.

In the present disclosure, a preferred first base agent is an amine, a metal hydride or a metal-aromatic compound coordination complex. Examples of an amine includes, without limitation, pyridine, triethylamine, 2,6-tert-butyl-pyridine, 2,6-tert-butyl-4-methyl-pyridine, and N,N,N',N'-tetramethyl-naphthalene-1,8-diamine and N-1-Naphthylethylenediamine. Examples of a metal hydride include, without limitation, sodium hydride and potassium hydride. Examples of a metal-aromatic compound coordination complex include, without limitation, Naphthalene$^-$.Li$^+$ (*Tetrahedron*, 66, 871, 2010; *Tetrahedron lett.*, 39, 4183, 1998.).

In step (b) of the process, the removal of the silyl ether protecting groups such as (—O—Si(R'$_{11}$)(R'$_{12}$)(R'$_{13}$), —O—Si(R'$_{21}$)(R'$_{22}$)(R'$_{23}$), and/or —O—Si(R'$_{31}$)(R'$_{32}$)(R'$_{33}$) is performed by using an acid or a fluoride. The acid is an inorganic acid (e.g. hydrochloric acid (HCl), hydrofluoric acid (HF), nitric acid, phosphoric acid, sulfuric acid, and boric acid) or an organic acid (e.g. camphorsulfonic acid (CSA) and acetic acid (AcOH)). The fluoride is tetra-n-butylammonium fluoride (TBAF) or hydrofluoric acid. In a preferred embodiment, the protecting group is removed in an acidic condition such as with an inorganic acid (e.g. HCl) in an alcohol (e.g. methanol and ethanol) at low temperature (e.g. lower than 5° C.; lower than 0° C.; −5~5° C.; or 0~5° C.), or at room temperature. The protecting group can also be removed by 100 mol % CSA in MeOH at room temperature; 10 mol % CSA, 1:1 MeOH:DCM, at −20; or 0° C.; 4:1:1 v/v/v AcOH:THF:water, at room temperature. The protecting group can also be removed in a basic condition such as HF in pyridine; 10:1 THF:pyridine at 0° C.; 1:1 TBAF/AcOH in THF; or TBAF in THF at room temperature.

In the present disclosure, examples of a preferred β-lactam include, without limitation, (3R,4S)-tert-butyl-2-oxy-4-phenyl-3-(triethylsilyloxy) azetidine-1-carboxylate, and (3R,4S)-phenyl-2-oxy-4-phenyl-3-(triethylsilyloxy) azetidine-1-carboxylate.

Examples of taxoids that can be prepared according to the present disclosure include, without limitation, (1S,2S,3R,4S,7R,9S,10S,12R,15S)-4,12-bis(acetyloxy)-1,9-dihydroxy-15-{[(2R,3S)-2-hydroxy-3-phenyl-3-(phenylformamido) propanoyl]oxy}-10,14,17,17-tetramethyl-11-oxo-6-oxatetracyclo[11.3.1.0$^{3,10}$.0$^{4,7}$]heptadec-13-en-2-yl benzoate (paclitaxel), (1S,2S,3R,4S,7R,9S,10S,12R,15S)-4-(acetyloxy)-15-{[(2R,3S)-3-{[(tert-butoxy)carbonyl]amino}-2-hydroxy-3-phenylpropanoyl]oxy}-1,9,12-trihydroxy-10,14,17,17-tetramethyl-11-oxo-6-oxatetracyclo [11.3.1.0$^{3,10}$.0$^{4,7}$]heptadec-13-en-2-yl benzoate (docetaxel), (1S,2S,3R,4S,7R,9S,11R,13R,16S)-4,13-bis(acetyloxy)-16-{[(2R,3S)-3-{[(tert-butoxy)carbonyl]amino}-2-hydroxy-3-phenylpropanoyl]oxy}-1-hydroxy-15,18,18-trimethyl-12-oxo-6-oxapentacyclo[12.3.1.0$^{3,11}$.0$^{4,7}$.0$^{9,11}$]octadec-14-en-2-yl benzoate (larotaxel), (1S,2S,3R,4S,7R,9S,10S,12R,15S)-4-(acetyloxy)-15-{[(2R,3S)-3-{[(tert-butoxy)carbonyl]amino}-2-hydroxy-3-phenylpropanoyl]oxy}-1-hydroxy-9,12-dimethoxy-10,14,17,17-tetra methyl-11-oxo-6-oxatetracyclo[11.3.1.0$^{3,10}$.0$^{4,7}$]heptadec-13-en-2-yl benzoate (cabazitaxel), and derivatives thereof.

II) A Process for Preparing a Protected Baccatin Derivative (B)

Another aspect of the present disclosure directs to a process for preparing a protected baccatin derivative (B), which can be used to prepare a taxoid (X).

In one embodiment, the process for preparing a protected baccatin derivative (B) comprises applying one or more Lewis acid M'L' and optionally a second base agent to a baccatin derivative (A) to form a protected baccatin derivative (B):

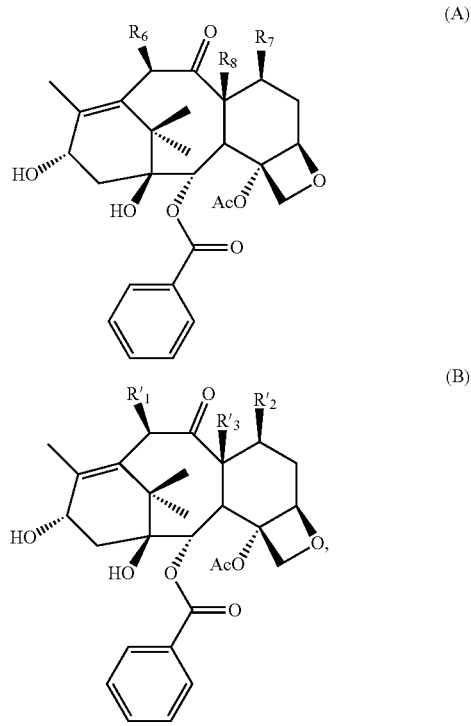

R'$_1$, R'$_2$, and R'$_3$ are defined the same as supra, preferably R'$_1$ is alkoxy and R'$_2$ is alkoxy, or R'$_1$ is —O—Si(R'$_{11}$)(R'$_{12}$) (R$_{13}$) and R'$_2$ is —O—Si(R'$_{21}$)(R'$_{22}$)(R'$_{23}$);

M' is selected from the group consisting of cations of Li, Na, K, Rb, Cs, Be, Mg, Ca, Sr, Ba, Cu, Ag, Au, Zn, Cd, Hg, Fe, Co, Ni, Ru, Rh, Pd, Os, Ir, Pt, Sc, Y, Ti, V, Nb, Co, B, Al, In, Sn, Ce, and any combination thereof;

L' is a counter ion;

R$_6$ is hydroxyl, alkoxy, aryloxy, —O—C(=O)—R$_{60}$, or —O—Si(R$_{61}$)(R$_{62}$)(R$_{63}$), and preferably hydroxyl;

R$_7$ is hydroxyl, alkoxy, aryloxy, —O—C(=O)—R$_{70}$, or —O—Si(R$_{71}$)(R$_{72}$)(R$_{73}$), and preferably hydroxyl or —O—Si(R$_{71}$)(R$_{72}$)(R$_{73}$), and more preferred hydroxyl or —O—Si(CH$_3$)$_3$ or —O—Si(C$_2$H$_5$)$_3$;

R$_8$ is alkyl, and preferably C$_{1-4}$alkyl such as methyl;

R$_{60}$, and R$_{70}$ are independently selected from the group consisting of hydrogen, hydroxyl, substituted and unsubstituted alkyl, and substituted and unsubstituted aryl; and R$_{61}$, R$_{62}$, R$_{63}$, R$_{71}$, R$_{72}$, and R$_{73}$ are independently selected from the group consisting of hydrogen, hydroxyl, substituted and unsubstituted alkyl, and substituted and unsubstituted aryl.

Examples of the baccatin derivative (A) include, without limitation, 10-DAB ($R_6$=$R_7$=H); 7,10-di-triethylsilyl-10-deacetylbaccatin III ($R_6$=$R_7$=—O—Si(CH$_2$CH$_3$)$_3$); (2α,3α,4α,5β,7α,10β,13α)-4,10-bis(acetyloxy)-1,13-dihydroxy-9-oxo-5,20-epoxy-7,19-cyclotax-11-en-2-yl benzoate ($R_6$=C(=O)CH$_3$, $R_7$=H); and 7,10-dimethoxy-10-deacetylbaccatin (III) ($R_6$=$R_7$=CH$_3$).

Examples of the second base agent include, without limitation, amine, metal hydride, or coordination complex of metal-aromatic compound. Preferably, the second base agent is pyridine, triethylamine, 2,6-tert-butyl-pyridine, 2,6-tert-butyl-4-methyl-pyridine, N,N,N',N'-tetramethyl-naphthalene-1,8-diamine, N-1-Naphthylethylenediamine, sodium hydride, potassium hydride, or Naphthalene-.Li+.

Optionally, the protected baccatin derivative (B) can be coupled with a β-lactam (C) in the presence of one or more Lewis acids ML and the first base agent to prepare a taxoid (X) as described supra, the first and the second base agents can be the same or different, and the Lewis acids ML and M'L' can be the same or different.

Comparing to the reaction carried out without Lewis acid, the presence of Lewis acid provides a more selective reaction, characterized by higher reaction rate, higher yield, more selective product, higher purity of the desired product and less side products. In certain embodiments, the presence of Lewis acid allows the reaction to happen at a less harsh condition, for example, using weaker base, at a lower reaction temperature, etc.

i) One-Step Di-Alkylation of C(7) and C(10)-OH

In a preferred embodiment, the baccatin derivative (A) is 10-DAB ($R_6$ and $R_7$ are hydroxyl, $R_8$ and $R'_3$ are methyl), and $R'_1$ and $R'_2$ are alkoxy. The process comprises reacting 10-DAB with an alkylation agent in the presence of a second base and/or one or more Lewis acids M'L' under suitable condition until a desired conversion of the protected baccatin derivative (B) has been achieved.

In a more preferred embodiment, $R'_1$ and $R'_2$ are methoxyl, and the alkylation agent is methyl sulfate (Me$_2$SO$_4$). Preferred second base agent include, without limitation, NaH, and Naphthalene-.Li+. Preferred L is a halogen (e.g. F, Cl, Br, or I). Preferred Lewis acid ML is selected from the group consisting of CsBr, KBr, MgBr$_2$, ZnBr$_2$, CeCl$_3$, and combinations thereof (e.g. CsBr and KBr; MgBr$_2$ and CsBr; ZnBr$_2$ and CsBr; and CeCl$_3$ and CsBr). Preferred combination of base and the one or more Lewis acids is selected from the group consisting of Naphthalene-.Li+ and CsBr, Naphthalene-.Li+ and KBr, NaH and CsBr, NaH and KBr, NaH and MgBr$_2$, NaH and ZnBr$_2$, NaH and CeCl$_3$, and combinations thereof (e.g. NaH, CsBr and KBr; NaH, MgBr$_2$ and CsBr; NaH, ZnBr$_2$ and CsBr; and NaH, CeCl$_3$ and CsBr). In certain embodiments, no base is present in the reaction.

ii) Two-Step Silylation of C(7) and C(10)-OH, Optionally a One-Pot Reaction

In another preferred embodiment, $R_6$ is hydroxyl, $R_8$ and $R'_3$ are methyl, and $R_7$, $R'_1$ and $R'_2$ are —O—Si(C$_2$H$_5$)$_3$. The process comprises reacting 10-DAB with a first silylation reagent to provide a first silylaton reaction mixture comprising the baccatin derivative (A) to be used in the reactions described supra.

Optionally, the process further comprises adding a second silylation reagent comprising the one or more Lewis acid M'L' into the first silylation reaction mixture to provide the protected baccatin derivative (B). Optionally, the first silylation reaction and the second silylation reaction are performed in the same reaction pot. Alternatively, the baccatin derivative (A) is isolated and purified to be used in the second silylation reaction as described supra. Preferably, $R'_{11}$, $R'_{12}$, $R'_{13}$, $R'_{21}$, $R'_{22}$, $R'_{23}$, $R_{71}$, $R_{72}$, and $R_{73}$ are independently —CH$_2$CH$_3$ or —CH$_3$.

Examples of silylaton reagent have been described supra. Preferred silylation reagent comprises trialkylsilyl halide (e.g. triethylsilyl chloride (TESCl)) and a base (e.g. triethylamine (NEt$_3$)). The second silylation reagent comprises one or more Lewis acid M'L' and optionally silylation reagent and/or the second base agent. Preferred Lewis acid M'L' includes, without limitation, LiBr, MgBr$_2$, CsBr, ZnBr$_2$, CuBr, and combinations thereof (e.g. CsBr and LiBr, ZnBr$_2$ and LiBr, CuBr and LiBr), preferred second base agent includes, without limitation, DMAP and NaH.

iii) Acylation of C(10)-OH

In another embodiment, the process for preparing a protected baccatin derivative (B) comprises a C(10)-acylation reaction. The process comprises;

1) reacting one or more Lewis acids M'L' and optionally a second base agent with a baccatin derivative (A) to under a suitable condition until a desired conversion of the first protected baccatin derivative (B⁰) has been achieved

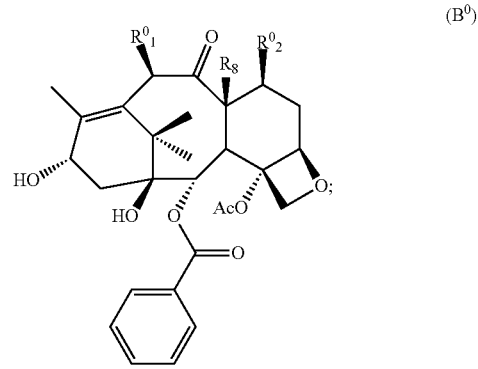

and 2) converting the first protected baccatin III derivative (B⁰) to the protected baccatin derivative (B), wherein:

M', L', $R_6$, $R_7$, $R_8$, $R'^1$, $R'_2$, $R'_3$, and the second base agent, are defined the same as supra;

$R^0_1$ is hydroxyl, alkoxy, aryloxy, —O—C(=O)—$R^0_{10}$, or —O—Si($R^0_{11}$)($R^0_{12}$)($R^0_{13}$), preferably —O—C(=O)—$R^0_{10}$, more preferably —O—C(=O)—CH$_3$;

$R^0_2$ is hydroxyl, alkoxy, aryloxy, —O—C(=O)—$R^0_{20}$, or —O—Si($R^0_{21}$)($R^0_{22}$)($R^0_{23}$), preferably hydroxyl;

$R^0_{10}$, and $R^0_{20}$ are independently selected from the group consisting of hydrogen, substituted and unsubstituted alkyl, and substituted and unsubstituted aryl; and $R^0_{11}$, $R^0_{12}$, $R^0_{13}$, $R^0_{21}$, $R^0_{22}$, and $R^0_{23}$ are independently selected from the group consisting of hydrogen, substituted and unsubstituted alkyl, and substituted and unsubstituted aryl.

Optionally, the protected baccatin derivative (B) can be coupled with a β-lactam (C) in the presence of one or more Lewis acids ML and the first base agent to prepare a taxoid (X) as described supra, the first and the second base agents can be the same or different, and the Lewis acids ML and M'L' can be the same or different.

In one preferred embodiment, $R'_2$ is hydrogen; and $R'_3$ is taken together with C7 to form a cycloalkyl ring, more preferably a cyclopropyl ring.

In another preferred embodiment, $R'_2$ is —O—Si($R'_{21}$)($R'_{22}$)($R'_{23}$); and preferably $R'_{21}$, $R'_{22}$, and $R'_{23}$ are independently ethyl or methyl.

Examples of the Lewis acids M'L' and the second base agents suitable in this process are the same as those described supra. In a preferred embodiment, L' is halogen (e.g. F, Cl, Br, or I). In another preferred embodiment, the one or more Lewis acids M'L' is selected from the group consisting of $ZnBr_2$, $LiBr$, $ZnCl_2$, $CuBr_2$ and combinations thereof (e.g. CuBr and LiBr, and CuBr and $ZnBr_2$). In certain embodiments, M' that forms a softer acid (e.g. $Zn^{2+}$ and $Cu^+$) provides better regioselectivity compared to M that forms a harder acid (e.g. $Li^+$) in catalyzing the C(10)-acetylation.

Comparing to the reaction carried out without Lewis acid, the presence of Lewis acid provides a more selective reaction, characterized by higher reaction rate, higher yield, more selective product, higher purity of the desired product and less side products. In certain embodiments, the presence of Lewis acid allows the reaction to happen at a less harsh condition, for example, using weaker base, at a lower reaction temperature, etc.

III) Preparation of Paclitaxel

The two key steps to prepare a taxol are the selective protection of 7- and 10-hydroxyl groups and the esterfication of 13-hydroxyl group.

In one embodiment, paclitaxel is prepared according to Scheme 1 that involves Lewis acid catalyzed regioselective protection and esterfication.

Scheme 1

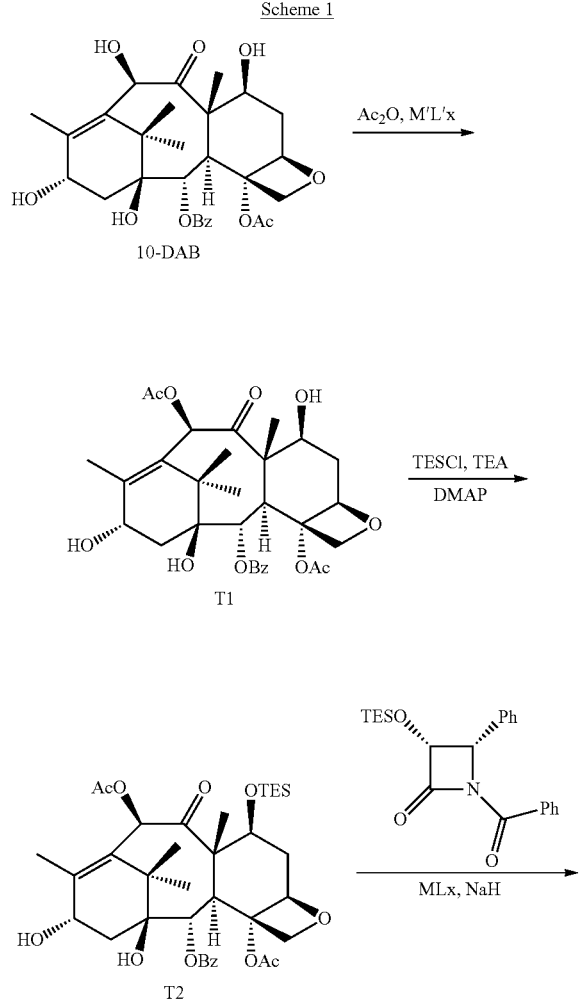

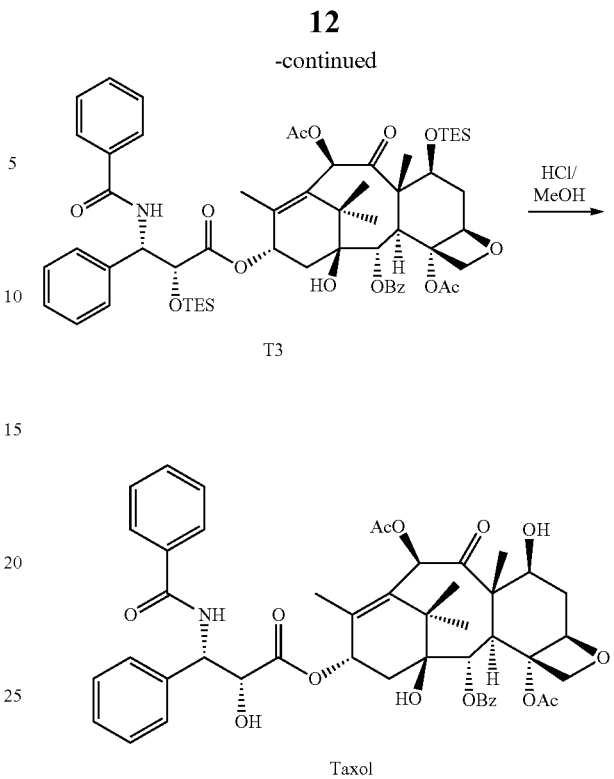

Taxol

As shown in Scheme 1, the baccatin derivative (A) is 10-DAB, the first protected baccatin derivative is baccatin III (T1), the protected baccatin derivative (B) is 7-O-TES-baccatin III (T2), the protected taxoid is 1-hydroxy-7β-triethylsilyloxy-9-oxo-10β-acetyloxy-5β,20-epoxytax-11-ene-2α, 4,13α-triyl 4-acetate 2-benzoate 13-[(2R,3S)-3-benzoylamino-2-trethylsilyloxy-3-phenylpropanoate] (T3), and T3 is further deprotected to afford paclitaxel (taxol).

The C(10)-OH of 10-DAB is regioselectively acetylated (C(10)-acetylation) by reacting with acetic anhydride catalyzed by one or more Lewis acids M'L'. In certain embodiments, L' is a halogen (e.g. F, Cl, Br, or I). In certain embodiments, the one or more Lewis acids M'L' is selected from the group consisting of $ZnBr_2$, $LiBr$, $ZnCl_2$, $CuBr_2$ and combinations thereof (e.g. CuBr and LiBr, and CuBr and $ZnBr_2$). In certain embodiments, M' that forms a softer acid (e.g. $Zn^{2+}$ and $Cu^+$) provides better regioselectivity compared to M' that forms a harder acid (e.g. $Li^+$) in catalyzing the C(10)-acetylation.

T1 is then silylated at C(7)-OH by triethylsilyl chloride, triethylamine and DMAP to produce T2.

The C(13)-OH of T2 is first deprotonated by sodium hydride, and then reacted with β-lactam catalyzed by one or more Lewis acids ML to obtain T3. In certain embodiments, L is a halogen (e.g. F, Cl, Br, or I). In certain embodiments, the one or more Lewis acids catalyst is selected from the group consisting of CsBr, KBr, $MgBr_2$, LiBr, $ZnBr_2$, and combinations thereof.

At last, T3 is deprotected by hydrochloric acid to produce paclitaxel (a taxol).

IV) Preparation of Larotaxel

In another embodiment, larotaxel is prepared according to Scheme 2 using Lewis acid catalyst to accelerate the esterfication reaction.

Scheme 2

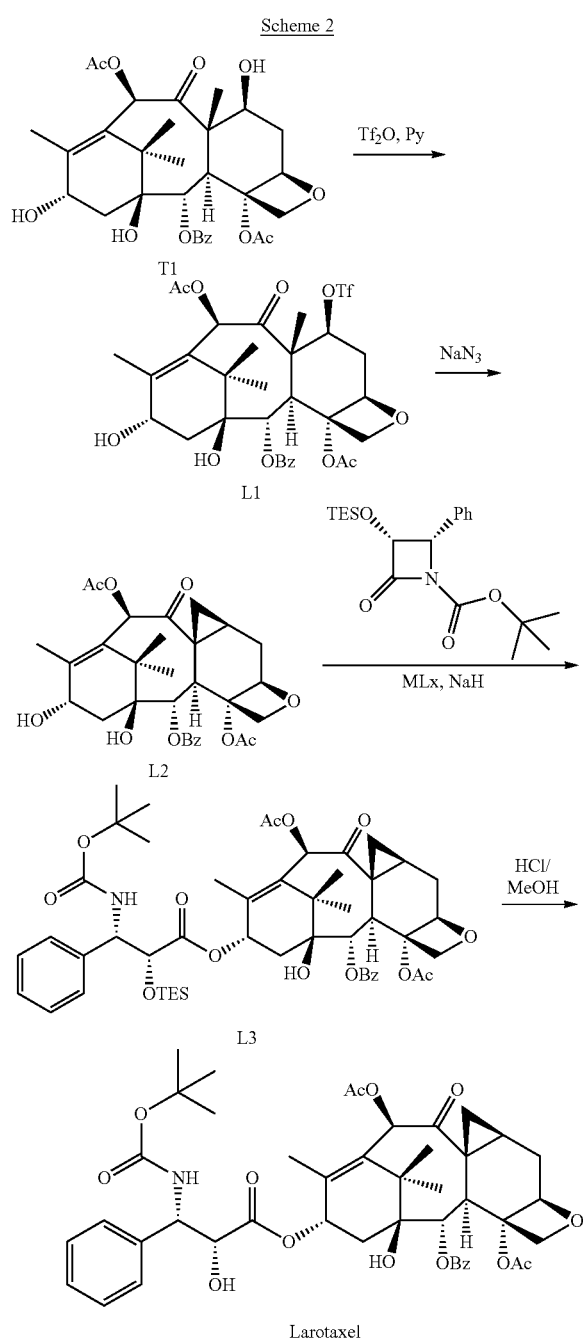

more Lewis acids ML to obtain L3. In certain embodiments, L is a halogen (e.g. F, Cl, Br, or I). In certain embodiments, the one or more Lewis acid catalyst is selected from the group consisting of CsBr, KBr, MgBr$_2$, LiBr, ZnBr$_2$, and combinations thereof.

At last, L3 is deprotected by hydrochloric acid to provide the final product, larotaxel.

V) Preparation of Docetaxel.

In another embodiment, docetaxel is prepared according to Scheme 3 that involves Lewis acid catalyzed regioselective protection and esterfication.

Scheme 3

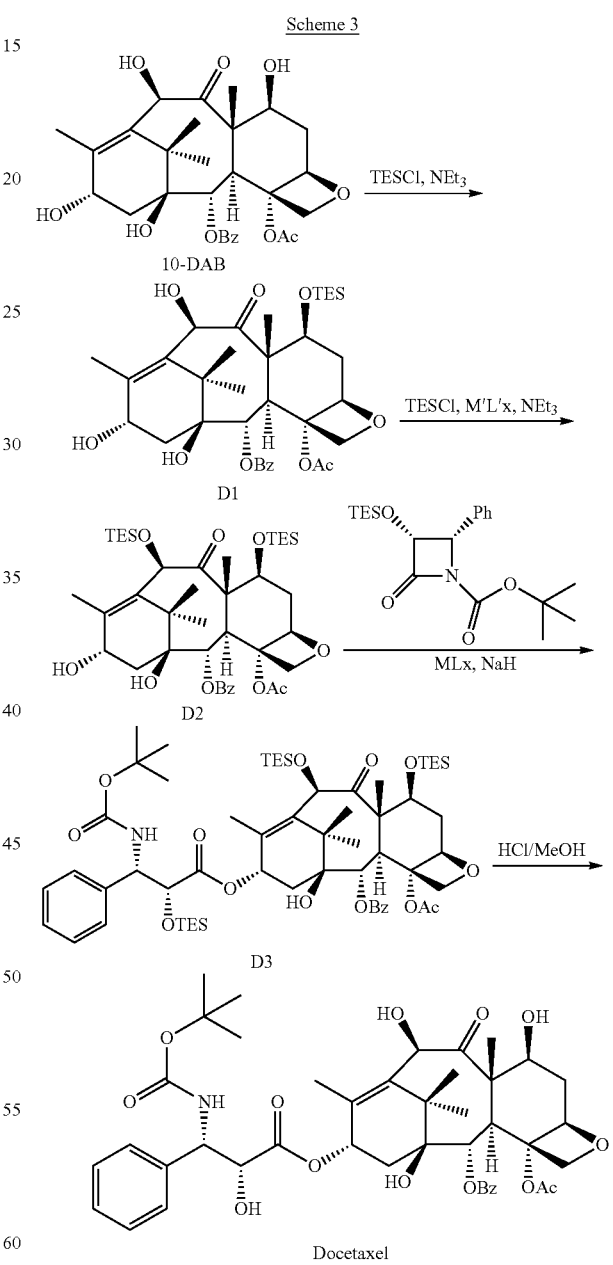

As shown in Scheme 2, the first protected baccatin derivative is T1, prepared from the baccatin derivative (A) 10-DAB as described supra, the protected baccatin derivative (B) is 7-O-triflate-baccatin III (L1), the esterfication of taxoid is (2α,3α,4α,5β,7α,10β,13α)-4,10-bis(acetyloxy)-13-({(2R, 3S)-3-[(tert-butoxycarbonyl)amino]-2-hydroxy-3-phenylpropanoyl}oxy)-1-hydroxy-9-oxo-5,20-epoxy-7,19-cyclotax-11-en-2-yl benzoate (L3), and L3 is further deprotected to afford the taxoid (X) larotaxel.

T1 is treated with triflic anhydride (Tf$_2$O) and pyridine to afford L1 (*Tetrahedron lett,* 35, 52, 9713, 1994), followed by treatment with sodium azide to obtain the cyploroyl intermediate L2. (*Tetrahedron Lett.,* 35, 43, 7893, 1994)

The C(13)-OH of L2 is first deprotonated by sodium hydride, and then reacted with β-lactam catalyzed by one or As shown in Scheme 3, the protected baccatin derivative (B) is 7,10-di-triethylsilyl-10-DAB (D2), prepared from the baccatin derivative (A) 7-O-TES-10-DAB (D1), the protected taxoid)(X°) is 1-hydroxy-7β,10β-di-triethylsilyloxy-9-oxo-5β,20-epoxytax-11-ene-2α,4,13α-triyl 4-acetate 2-benzoate 13-{(2R,3S)-3-[(tert-butoxycarbonyl)amino]-2-trethylsilyloxy-3-phenylpropanoate} (D3), and D3 is further deprotected to afford the taxoid (X) docetaxel.

D1 is provided by regioselective silylation of C(7)-OH of 10-DAB with triethylsilyl chloride (TESCl) and triethylamine (NEt$_3$).

In certain embodiments, the two-step silylation reaction of C(7) and C(10)-OH of 10-DAB can be completed in a one-pot reaction. One or more Lewis acids M'L' is added to the reaction mixture after the completion of the silylation of C(7)-OH to carry out the silylation of C(10)-OH without purification of D1. In certain embodiments, L' is a halogen (e.g. F, Cl, Br, or I). In certain embodiments, the one or more Lewis acid catalyst is selected from the group consisting of LiBr, MgBr$_2$, CsBr, ZnBr$_2$, CuBr, and combinations thereof (e.g. LiBr and CsBr; ZnBr$_2$ and LiBr; and CuBr and LiBr).

The C(13)-OH of D2 is first deprotonated by sodium hydride, and then reacted with β-lactam catalyzed by one or more Lewis acids ML to provide D3. In certain embodiments, L is a halogen (e.g. F, Cl, Br, or I). In certain embodiments, the one or more Lewis acid catalyst is selected from the group consisting of LiBr, MgBr$_2$, CsBr, CsCl$_3$ and combinations thereof.

At last, D3 is deprotected by hydrochloric acid to provide the final product, docetaxel.

VI) Preparation of Cabazitaxel.

In another embodiment, cabazitaxel is prepared according to Scheme 4 that involves Lewis acid catalyzed regioselective protection and esterfication.

Scheme 4

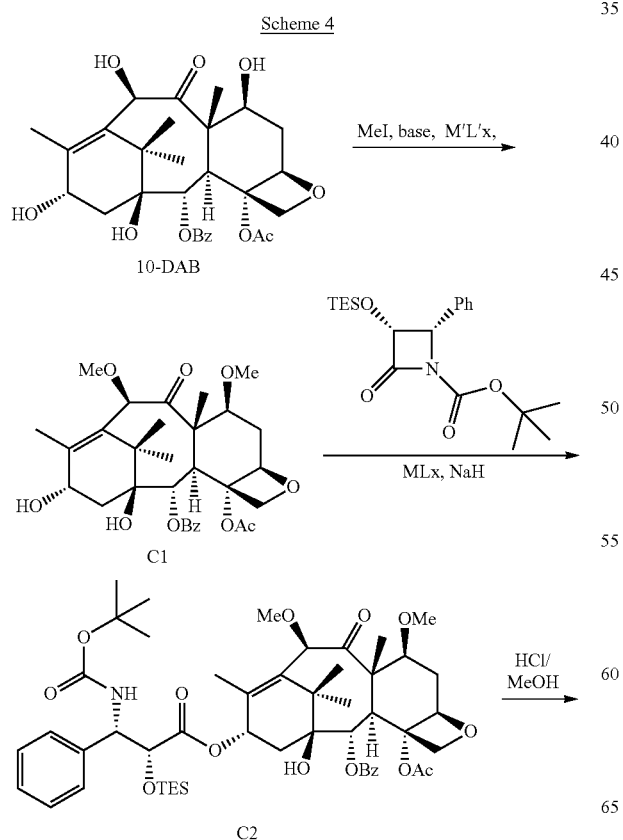

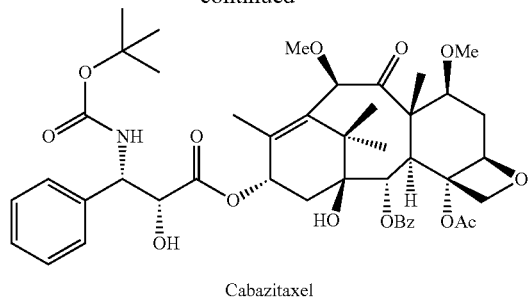

Cabazitaxel

As shown in Scheme 4, the protected baccatin derivative (B) is 7,10-di-methoxyl-10-DAB (C1), prepared from the first baccatin derivative (A) 10-DAB, the protected taxoid) (X$^0$) is 1-hydroxy-7β,10β-di-methoxy-9-oxo-5β,20-epoxytax-11-ene-2α,4,13α-triyl 4-acetate 2-benzoate 13-{(2R, 3S)-3-[(tert-butoxycarbonyl)amino]-2-trethylsilyloxy-3-phenylpropanoate} (C2), and C2 is further deprotected to afford the taxoid (X) cabazitaxel.

10-DAB is reacted with methyl sulfate (Me$_2$SO$_4$) in the presence of a base and/or one or more Lewis acids M'L' to provide C1. In certain embodiments, L' is a counter ion such as an anion of a halogen (e.g. F, Cl, Br, or I). In certain embodiments, the one or more Lewis acid catalyst is selected from the group consisting of CsBr, KBr, MgBr$_2$, ZnBr$_2$, CeCl$_3$, and combinations thereof (e.g. CsBr and KBr; MgBr$_2$ and CsBr; ZnBr$_2$ and CsBr; and CeCl$_3$ and CsBr). In certain embodiments, the base is Naphthalene$^-$.Li$^+$. In certain embodiments, the combination of base and one or more Lewis acid catalyst is selected from the group consisting of Naphthalene$^-$.Li$^+$ and CsBr, and Naphthalene$^-$.Li$^+$ and KBr. In certain embodiments, no base is present in the reaction. In certain embodiments, both base and the one or more Lewis acids are present in the reaction.

The C(13)-OH of C1 is first deprotonated by sodium hydride, and then reacted with β-lactam catalyzed by one or more Lewis acids ML to obtain C2. In certain embodiments, L is a halogen (e.g. F, Cl, Br, or I). In certain embodiments, the one or more Lewis acid catalyst is selected from the group consisting of LiBr, MgBr$_2$, CsBr, CsCl$_3$, KBr, FeCl$_3$, and combinations thereof.

At last, C2 is deprotected by hydrochloric acid to provide the final product cabazitaxel.

The following examples further illustrate the present disclosure. These examples are intended merely to be illustrative of the present disclosure and are not to be construed as being limiting.

EXAMPLES

I. Synthesis of 7,10-di-triethylsilyl-10-deacetylbaccatin (III) (D2) Using Lewis Acid Catalysts (LiBr, MgBr$_2$, CsBr/LiBr, ZnBr$_2$/LiBr, and CuBr/LiBr) (Examples 1-5)

Example 1

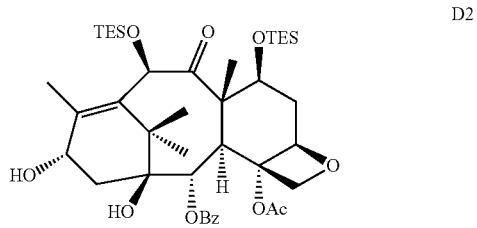

Preparation of 7,10-di-triethylsilyl-10-deacetylbaccatin (III) (D2) Catalyzed by LiBr To a solution of 10-DAB (10 g) and DMAP (1 eq, 2.2 g) in 200 mL of THF at 25° C. under nitrogen was added triethylamine (18 eq, 45.8 mL) and TESCl (8 eq, 25 mL) dropwise and was kept stirred for 3 to 4 hours. After the consumption of 10-DAB, LiBr (1 eq, 1.6 g) in 10 mL THF was added to the reaction mixture. The reaction was stirred at 65~70° C. for 3~5 hours and then stirred at 20~30° C. for following 13~16 hours until the reaction is completed. The reaction solution was diluted with 200 mL ethylacetate and washed with 200 mL water. After partition, the organic layer was dried by rotavapor. The crude D2 obtained after evaporation was digested with 120 mL n-hexane for 3~4 hour. Finally, the product (yield 89%, 12.6 g, LC purity 98%), 7,10-di-triethylsilyl-10-deacetylbaccatin (III), dried under vacuum after filtration was obtained. $^1$H NMR (CDCl$_3$, 400 MHz) δ 8.10 (d, J=7.6 Hz, 2H), 7.58 (t, J=7.6 Hz, 1H), 7.46 (t, J=7.6 Hz, 2H), 5.61 (d, J=7.1 Hz, 1H), 5.21 (s, 1H), 4.93 (dd, J=1.7, 9.3 Hz, 1H), 4.82 (m, 1H), 4.42 (dd, J=6.6, 10.4 Hz, 1H), 4.27 (d, J=8.2 Hz, 1H), 4.14 (d, J=8.2 Hz, 1H), 3.91 (d, J=6.6 Hz, 1H), 2.53-2.41 (m, 1H), 2.27 (s, 3H), 2.25 (m, 2H), 2.03 (s, 3H), 2.01-1.95 (m, 1H), 1.85 (m, 1H), 1.64 (s, 3H), 1.18 (s, 3H), 1.04 (s, 3H), 1.02-0.85 (m, 18H), 0.69-0.58 (m, 12H); $^{13}$C NMR (CDCl$_3$, 100 MHz) δ 205.7, 170.8, 167.1, 137.7, 136.9, 133.4, 130.0, 129.5, 128.5, 84.0, 80.9, 78.7, 75.8, 74.9, 72.8, 67.9, 58.6, 47.2, 42.7, 38.3, 37.3, 26.7, 22.7, 19.4, 14.6, 10.3, 6.9, 6.8, 5.8, 5.3.

Example 2

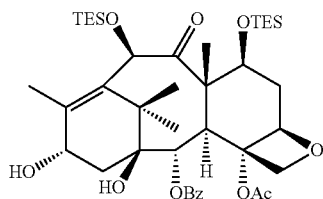

D2

Preparation of 7,10-di-triethylsilyl-10-deacetylbaccatin (III) (D2) Catalyzed by MgBr$_2$ To a solution of 7-triethylsilyl-10-deacetylbaccatin (III) (D1, 1 eq) and MgBr$_2$ (0.5 eq) in THF after stirred for 30 minutes at 25° C. under nitrogen was added DMAP (0.5 eq), triethylamine (8 eq) and TESCl (4 eq) dropwise. The reaction was stirred under reflux for 46.5 hours. The reaction solution was diluted with ethylacetate and washed with water. After partition, the organic layer was dried by rotavapor to obtain the crude D2 (LC purity 48%).

Example 3

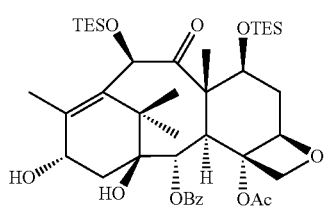

D2

Preparation of 7,10-di-triethylsilyl-10-deacetylbaccatin (III) (D2) Catalyzed by a Mixture of CsBr and LiBr To a solution of 7-triethylsilyl-10-deacetylbaccatin (III) (D1, 1 eq), CsBr (0.5 eq) and LiBr (0.5 eq) in THF after stir for 30 minutes at 25° C. under nitrogen was added DMAP (0.5 eq), triethylamine (8 eq) and TESCl (4 eq) dropwise. The reaction was stirred under reflux for 46.5 hours. The reaction solution was diluted with ethylacetate and washed with water. After partition, the organic layer was dried by rotavapor to obtain the crude D2 (LC purity 78%).

Example 4

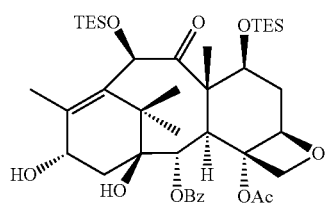

D2

Preparation of 7,10-di-triethylsilyl-10-deacetylbaccatin (III) (D2) Catalyzed by a Mixture of ZnBr$_2$ and LiBr To a solution of 7-triethylsilyl-10-deacetylbaccatin (III) (D1, 1 eq), ZnBr$_2$ (0.5 eq) and LiBr (0.5 eq) in THF after stir for 30 minutes at 25° C. under nitrogen was added DMAP (0.5 eq), triethylamine (8 eq) and TESCl (4 eq) dropwise. The reaction was stirred under reflux for 46.5 hours. The reaction solution was diluted with ethylacetate and washed with water. After partition, the organic layer was dried by rotavapor to obtain the crude D2 (LC purity 58%).

Example 5

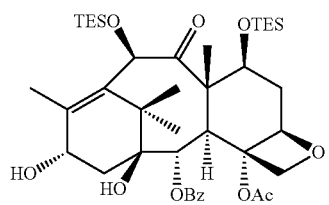

D2

Preparation of 7,10-di-triethylsilyl-10-deacetylbaccatin (III) (D2) Catalyzed by a Mixture of CuBr and LiBr To a solution of 7-triethylsilyl-10-deacetylbaccatin (III) (D1, 1 eq), CuBr (0.5 eq) and LiBr (0.5 eq) in THF after stir for 30 minutes at 25° C. under nitrogen was added DMAP (0.5 eq), triethylamine (8 eq) and TESCl (4 eq) dropwise. The reaction was stirred under reflux for 46.5 hours. The reaction solution was diluted with ethylacetate and washed with water.

After partition, the organic layer was dried by rotavapor to obtain the crude D2 (LC purity 26%).

II. Synthesis of 1-hydroxy-7β,10β-di-triethylsilyloxy-9-oxo-5β,20-epoxytax-11-ene-2α,4,13α-triyl 4-acetate 2-benzoate 13-{(2R,3S)-3-[(tert-butoxycarbonyl)amino]-2-trethylsilyloxy-3-phenylpropanoate} (D3) Using Lewis Acid Catalysts (LiBr, MgBr$_2$, CsBr, and CeCl$_3$) (Examples 6-9)

Example 6

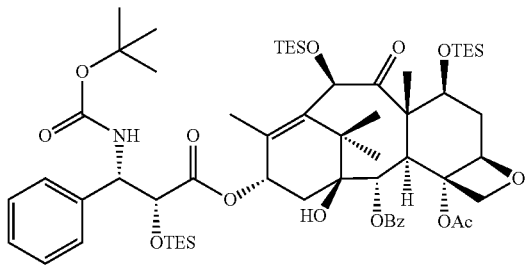

D3

Preparation of 1-hydroxy-7β,10β-di-triethylsilyloxy-9-oxo-5β,20-epoxytax-11-ene-2α,4,13α-triyl 4-acetate 2-benzoate 13-{(2R,3S)-3-[(tert-butoxycarbonyl)amino]-2-trethylsilyloxy-3-phenylpropanoate} (D3) by the catalyst of LiBr To a solution of sodium hydride (60%, 8 eq, 0.2 g,) in 5 mL THF cooled to −15~−10° C. under nitrogen was dropwise added a solution of 7,10-di-triethylsilyl-10-DAB (D2, 0.5 g) in 5 mL THF. The reaction mixture was stirred at −5~5° C. for 1 hour and then added a solution of (3R,4S)-tert-butyl 2-oxy-4-phenyl-3-(triethylsilyloxy)azetidine-1-carboxylate (β-lactam, 2.6 eq, 0.63 g) in 3 mL THF dropwise. After stirred at −5~5° C. for 1 hour, the reaction mixture was added a solution of LiBr (1 eq, 0.06 g) in 2 mL THF. The reaction mixture was stirred for 3 hours until the reaction was completed. The reaction was neutralized with 5 mL 10% AcOH/THF at −5~5° C., and then was diluted with 20 mL ethylacetate and washed with 20 mL saturated sodium bicarbonate. The organic layer was dried by rotavapor to obtain the crude D3 (LC purity 96%).

Example 7

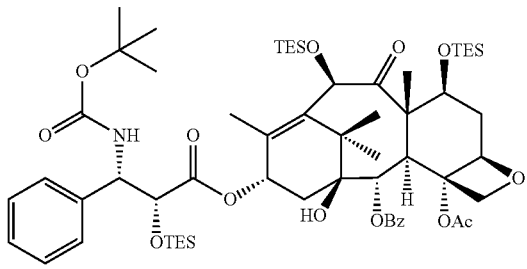

D3

Preparation of 1-hydroxy-7β,10β-di-triethylsilyloxy-9-oxo-5β,20-epoxytax-11-ene-2α,4,13α-triyl 4-acetate 2-benzoate 13-{(2R,3S)-3-[(tert-butoxycarbonyl)amino]-2-trethylsilyloxy-3-phenylpropanoate} (D3) by the catalyst of CsBr To a solution of sodium hydride (60%, 8 eq, 83 mg,) in 2 mL THF cooled to −15~−10° C. under nitrogen was added a solution of 7,10-di-triethylsilyl-10-DAB (D2, 200 mg) in 2 mL THF dropwise. The reaction mixture was stirred at −5~5° C. for 1 hour and then added a solution of (3R,4S)-tert-butyl 2-oxy-4-phenyl-3-(triethylsilyloxy)azetidine-1-carboxylate (β-lactam, 2.5 eq, 244 mg) in 3 mL THF dropwise. The reaction mixture was stirred at −5~5° C. for 1 hour, and then added a solution of CsBr (0.5 eq, 28 mg) in 2 mL THF. The reaction mixture was stirred for 3 hours until the reaction was completed. The reaction was neutralized with 5 mL 10% AcOH/THF at −5~5° C., diluted with 20 mL ethyl acetate and washed with 20 mL saturated sodium bicarbonate. The organic layer was dried by rotavapor to obtain the crude D3 (LC purity 94%).

Example 8

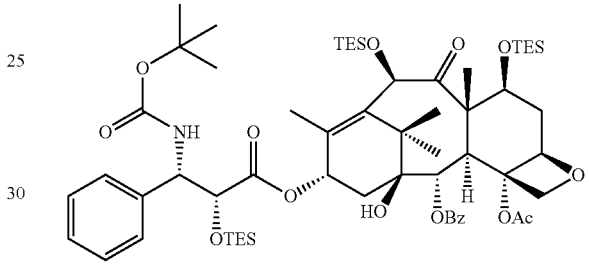

D3

Preparation of 1-hydroxy-7β,10β-di-triethylsilyloxy-9-oxo-5β,20-epoxytax-11-ene-2α,4,13α-triyl 4-acetate 2-benzoate 13-{(2R,3S)-3[(tert-butoxycarbonyl)amino]-2-trethylsilyloxy-3-phenylpropanoate} (D3) by the catalyst of MgBr$_2$ To a solution of sodium hydride (60%, 8 eq, 82.9 mg,) in 2 mL THF cooled to −5° C. under nitrogen was dropwise added a solution of 7,10-di-triethylsilyl-10-DAB (D2, 1 eq, 200 mg) in 2 mL THF. The reaction mixture was stirred at −5° C. for 1 hour and then dropwise added a solution of (3R,4S)-tert-butyl 2-oxy-4-phenyl-3-(triethylsilyloxy)azetidine-1-carboxylate (β-lactam, 2.5 eq, 244 mg) and MgBr$_2$ (0.5 eq, 23.9 mg) in 2 mL THF. The reaction mixture was stirred for 3 hours until the reaction was completed. The reaction was quenched with 10% AcOH/THF, and extracted with ethylacetate and water. The organic layer was dried by rotavapor to obtain the crude D3 (LC purity 43%).

Example 9

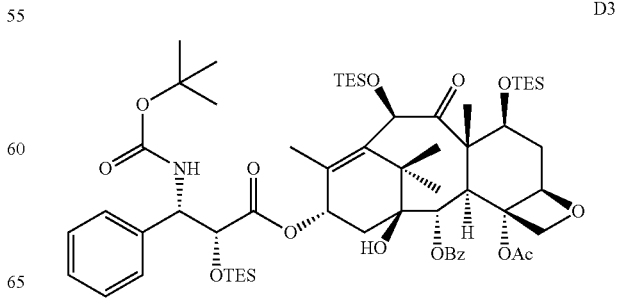

D3

Preparation of 1-hydroxy-7β,10β-di-triethylsilyloxy-9-oxo-5β,20-epoxytax-11-ene-2α,4,13α-triyl 4-acetate 2-benzoate 13-{(2R,3S)-3-[(tert-butoxycarbonyl)amino]-2-trethylsilyloxy-3-phenylpropanoate} (D3) by the catalyst of CeCl₃

To a solution of sodium hydride (60%, 8 eq, 83 mg) in 2 mL THF cooled to −5° C. under nitrogen was dropwise added a solution of 7,10-di-triethylsilyl-10-DAB (D2, 1 eq, 200 mg) in 2 mL THF. The reaction mixture was stirred at −5° C. for 1 hour and then added a solution of (3R,4S)-tert-butyl 2-oxy-4-phenyl-3-(triethylsilyloxy)azetidine-1-carboxylate (β-lactam, 2.5 eq, 244 mg) and CeCl₃ (0.5 eq, 32.0 mg) in 2 mL THF dropwise. The reaction mixture was stirred for 3 hours until the reaction was completed. The reaction was quenched with 10% AcOH/THF, and extracted with ethylacetate and water. The organic layer was dried by rotavapor to obtain the crude D3 (LC purity 26%).

Example 10

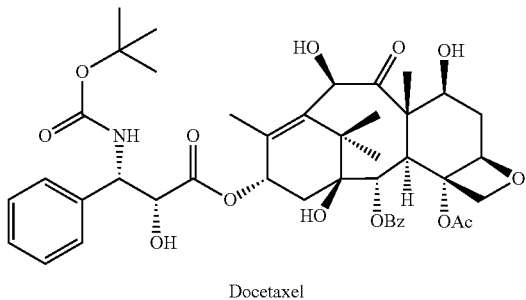

Docetaxel

Preparation of (1S,2S,3R,4S,7R,9S,10S,12R,15S)-4-(acetyloxy)-15-{[(2R,3S)-3-{[(tert-butoxy)carbonyl]amino}-2-hydroxy-3-phenylpropanoyl]oxy}-1,9,12-trihydroxy-10,14,17,17-tetramethyl-11-oxo-6-oxatetracyclo[11.3.1.0³,¹⁰.0⁴,⁷]heptadec-13-en-2-yl benzoate (docetaxel)

The crude D3 of EXAMPLE 6 in 22.5 mL MeOH was added 0.09 mL 32% HCl$_{(aq)}$ at −5~5° C. stirred for 3 hours. Then the reaction temperature was raised to 20~30° C., and the reaction mixture was stirred for 24 hours until the deprotection was completed. The reaction mixture was dried by rotavapor and then diluted with 40 mL CH₂Cl₂. After washed with 40 mL saturated sodium bicarbonate, the organic layer was dried by rotavapor to obtain the crude of docetaxel. The crude docetaxel in 10 mL CH₂Cl₂ was slowly added 5 mL n-Heptane to let docetaxel precipitate. After filtration and dried the solid, 0.3 g docetaxel (yield 60%, LC purity 96%) was obtained. ¹H NMR (400 MHz, CDCl₃) δ, 7.50-8.12 (5H), 7.38 (5H), 6.22 (t, J=9.0 Hz, 1H), 5.68 (d, J=7.0 Hz, 1H), 5.46 (d, J=9.0 Hz, 1H), 5.26 (dd, J=9.0 and 2.0 Hz, 1H), 5.22 (s, 1H), 4.32 (d, J=9.0 Hz, 1H), 4.19 (d, J=9.0 Hz, 1H), 3.91 (d, J=7.0 Hz, 1H), 2.58-2.45 (m, 1H), 2.37 (s, 3H), 2.28-2.20 (m, 2H), 1.87 (s, 3H), 1.77 (s, 3H), 1.35 (s, 9H), 1.24 (s, 3H), 1.12 (s, 3H); ¹³C NMR (100 MHz, CDCl₃) δ 212.0, 171.0, 167.7, 156.0, 139.1, 136.5, 134.4, 130.8, 129.7, 129.5, 129.4, 128.7, 127.4, 84.8, 81.7, 80.9, 79.4, 75.4, 75.2, 74.3, 73.1, 72.6, 58.3, 56.8, 47.1, 43.7, 37.6, 36.3, 30.3, 30.0, 29.9, 28.8, 27.1, 23.2, 21.3, 15.0, 10.5.

III. Synthesis of 10-acetyl-10-deacetylbaccatin (III) (T1) Using Lewis Acid Catalysts (ZnBr₂, LiBr, ZnCl₂, CuBr, CuBr/LiBr, and CuBr/ZnBr₂) (Examples 11-16)

Example 11

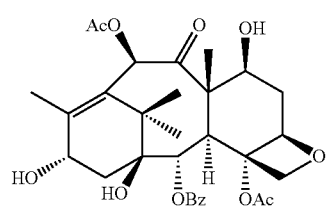

Preparation of 10-acetyl-10-deacetylbaccatin (III) T1 Catalyzed by ZnBr₂

To a solution of 10-DAB (1.0 g) in 20 mL THF was slowly added a solution of ZnBr₂ (2 eq, 0.21 g) in 0.4 mL THF, and then was added acetic anhydride (6 eq, 1.0 mL). Then, the reaction temperature was raised to 60° C. and stirred for 19 hours. The reaction mixture was diluted with ethylacetate and washed by water. After partition, the organic layer was dried by magnesium sulfate. After filtration, the filtrate was evaporated and purified by chromatography to produce T1 (yield 73%, 830 mg, LC purity 95%). ¹H NMR (400 MHz, CDCl₃) δ 8.12-8.19 (m, 2H), 7.63-7.59 (m, 1H), 7.5-7.47 (m, 2H), 6.33 (s, 1H), 5.62 (d, J=6.8 Hz, 1H), 4.99 (dd, J=9.6, 2.0 Hz, 1H), 4.89 (t, J=7.8 Hz, 1H), 4.47 (dd, J=6.8, 10.8 Hz, 1H), 4.31 (d, J=8.4 Hz, 1H), 4.16 (d, J=8.4 Hz, 1H), 3.88 (d, J=7.2 Hz, 1H), 2.60-2.53 (m, 2H), 2.31-2.29 (m, 2H), 2.29 (s, 3H), 2.25 (s, 3H), 2.06 (d, J=1.2 Hz, 3H), 1.87 (ddd, J=10.8, 13.9, 2.0 Hz, 1H), 1.67 (s, 3H), 1.11 (s, 6H); ¹³C NMR (100 MHz, CDCl₃) δ 204.3, 171.4, 170.7, 167.0, 146.7, 133.7, 131.6, 130.1, 129.3, 128.7, 84.5, 80.7, 79.0, 76.4, 76.3, 74.9, 72.3, 67.8, 58.6, 46.1, 42.8, 38.7, 35.6, 26.9, 22.6, 20.9 15.6, 9.5.

Example 12

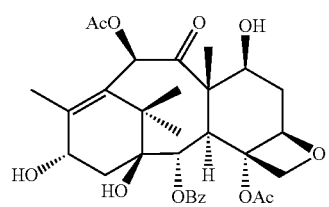

Preparation of 10-acetyly-10-deacetylbaccatin (III) T1 Catalyzed by LiBr

To a solution of 10-DAB (10.0 g) in 200 mL THF was slowly added a solution of LiBr (1 eq, 1.56 g) in 4 mL THF, and then was added acetic anhydride (6 eq, 1.76 mL). Then, the reaction temperature was raised to 60° C. and the reaction mixture was stirred for 17 hours. The reaction mixture was diluted with ethyl acetate and washed by water. After partition, the organic layer was dried by magnesium sulfate. After filtration, the filtrate was evaporated to produce crude T1 (yield 50%; 8.3 g, LC purity of product 65%).

Example 13

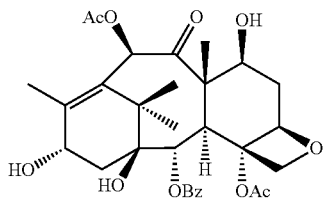

T1

Preparation of 10-acetyly-10-deacetylbaccatin (III) T1 Catalyzed by $ZnCl_2$

To a solution of 10-DAB (0.25 g) in 5 mL THF was slowly added a solution of $ZnCl_2$ (0.5 eq, 0.03 g) in 0.5 mL THF, and then was added acetic anhydride (1.5 eq, 0.06 mL). Then, the reaction temperature was raised to 60° C. and the reaction mixture was stirred for 17 hours. The reaction mixture was diluted with ethylacetate and washed by water. After partition, the organic layer was dried by magnesium sulfate. After filtration, the filtrate was evaporated to produce crude T1 (yield 74%; 240 mg, LC purity of product, 83%).

Example 14

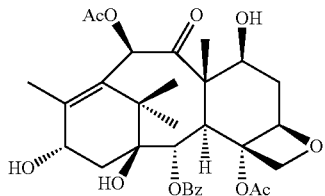

T1

Preparation of 10-acetyly-10-deacetylbaccatin (III) T1 Catalyzed by CuBr

To a solution of 10-DAB (0.5 g) in 10 mL THF was slowly added a solution of CuBr (0.5 eq, 0.07 g) in 3 mL THF, and then was added acetic anhydride (5 eq, 0.440 mL). Then, the reaction temperature was raised to 60° C. and the reaction mixture was stirred for 21.5 hours. The reaction mixture was diluted with ethylacetate and washed by water. After partition, the organic layer was dried by magnesium sulfate. After filtration, the filtrate was evaporated to produce crude T1 (yield 60%; 360 mg, LC purity of product, 89%).

Example 15

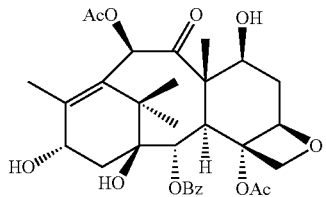

T1

Preparation of 10-acetyly-10-deacetylbaccatin (III) T1 Catalyzed by the Mixture of CuBr and LiBr To a solution of 10-DAB (0.5 g) in 10 mL THF was slowly added a solution of CuBr (0.5 eq, 0.07 g) and LiBr (0.5 eq, 0.04 g) in 3 mL THF, and then was added acetic anhydride (5 eq, 0.440 mL). The reaction temperature was raised to 60° C. and the reaction, mixture was stirred for 21.5 hours. The reaction, mixture was diluted with ethylacetate and washed by water. After partition, the organic layer was dried by magnesium sulfate. After filtration, the filtrate was evaporated to produce crude T1 (LC purity 91%).

Example 16

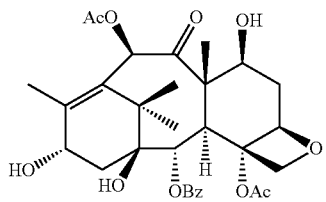

T1

Preparation of 10-acetyly-10-deacetylbaccatin (III) (T1) Catalyzed by the Mixture of CuBr and $ZnBr_2$ To a solution of 10-DAB (0.5 g) in 10 mL THF was added a solution of CuBr (0.5 eq, 0.07 g) and $ZnBr_2$ (0.5 eq, 0.1 g) in 3 mL THF, and then was added acetic anhydride (5 eq, 0.440 mL). Then, the reaction temperature was raised to 60° C. and the reaction mixture was stirred for 21.5 hours. Then the reaction mixture was diluted with ethylacetate and washed by water. After partition, the organic layer was dried by magnesium sulfate. After filtration, the filtrate was evaporated to produce crude T1 (yield 75%; 420 mg, LC purity, 97° A)).

IV. Synthesis of 1-hydroxy-7β-triethylsilyloxy-9-oxo-10β-acetyloxy-5β,20-epoxytax-11-ene-2α,4,13α-triyl 4-acetate 2-benzoate 13-[(2R,3S)-3-benzoylamino-2-trethylsilyloxy-3-phenylpropanoate] (T3) using Lewis acid catalysts (CsBr, KBr, $MgBr_2$, LiBr, and $ZnBr_2$) (Examples 17-21)

Example 17

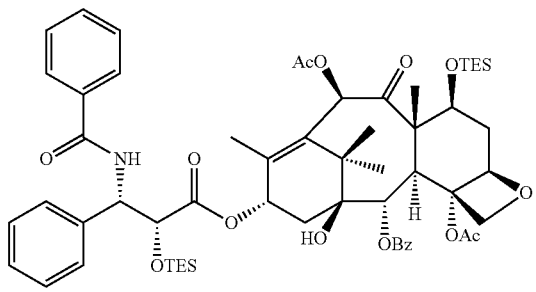

T3

Preparation of 1-hydroxy-7β-triethylsilyloxy-9-oxo-10β-acetyloxy-5β,20-epoxytax-11-ene-2α,4,13α-triyl 4-acetate 2-benzoate 13-[(2R,3S)-3-benzoylamino-2-trethylsilyloxy-3-phenylpropanoate] (T3) by the catalyst of CsBr A solution of 10-deacetylbaccatin (III) T1 (1 eq, 10.0 g, LC purity 97%) in THF was stirred for 30 minutes at 25° C. under nitrogen, then was added DMAP (1.4 eq, 3 g), triethylamine (12 eq, 28.5 mL) and TESCl (5.1 eq, 13.1 g) slowly. The reaction was stirred under reflux for 16 hours, diluted with ethylacetate and washed with water. After partition, the organic layer was dried by rotavapor to obtain the crude T2 (yield 75%, 9.5 g, LC purity 92%).

A solution of sodium hydride (60%, 5.6 eq, 320 mg) in 0.5 mL THF was cooled to −5~0° C. under nitrogen, and into which a solution of the crude T2 in THF (1 eq, 100 mg/L) was slowly added. The reaction mixture was stirred at −5~0° C. for 0.5 hour, and then added dropwise a mixture of (3R,4S)-1-benzoyl-4-phenyl-3-(triethylsilyl)oxy-2-azetidinone (β-lactam, 2 eq, 109 mg) and CsBr (1 eq, 30 mg) in 0.5 mL THF. The reaction was stirred at 0~7° C. for 2 hours until the reaction was completed. The reaction was neutralized with 2 mL 10% AcOH/THF at 0~5° C., and then diluted with 5 mL ethyl acetate and washed with 5 mL saturated sodium bicarbonate. The organic layer was dried by rotavapor to obtain the crude T3 (yield 75%, 154 mg, LC purity 69%). $^1$H NMR (400 MHz, CDCl$_3$) δ 8.11 (d, J=7.0 Hz, 2H), 7.72 (d, J=7.5, 2H), 7.60-7.25 (band, 11H), 7.05 (d, J=9.0 Hz, 1H, NH), 6.43 (s, 1H), 6.22 (t, J=8.5 Hz, 1H), 5.69-5.55 (m, 2H), 4.93 (d, J=8.0 Hz, 1H), 4.69 (d, J=2.0 Hz, 1H), 4.45 (dd, J=11.0, 7.0 Hz, 1H), 4.30 (d, J=8.5 Hz, 1H), 4.19 (d, J=8.5 Hz, 1H), 3.82 (d, J=7.0 Hz, 1H), 2.53 (s, 3H), 2.38 (dd, J=9.5, 15.0 Hz, 1H), 2.18 (s, 3H), 2.12 (dd, J=15.0, 8.0 Hz, 1H), 2.00 (s, 3H), 1.89-1.75 (m, 2H), 1.68 (s, 3H), 1.20 (s, 3H), 1.16 (s, 3H), 0.89 (t, J=8.0 Hz, 9H), 0.80 (t, J=8.0 Hz, 9H), 0.62-0.35 (band, 12H); $^{13}$C NMR (100 MHz, CDCl$_3$) δ 201.7, 171.5, 170.0, 169.3, 167.0, 140.1, 138.4, 134.0, 133.69, 133.62, 131.7, 130.2, 129.2, 128.6, 127.9, 127.0, 126.4, 84.2, 81.1, 78.8, 74.98, 74.94, 74.8, 72.2, 71.4, 58.4, 55.6, 46.6, 43.3, 37.2, 35.5, 26.5, 23.0, 21.4, 20.8, 14.1, 10.1, 6.7, 6.5, 5.2, 4.3, 1.0.

Example 18

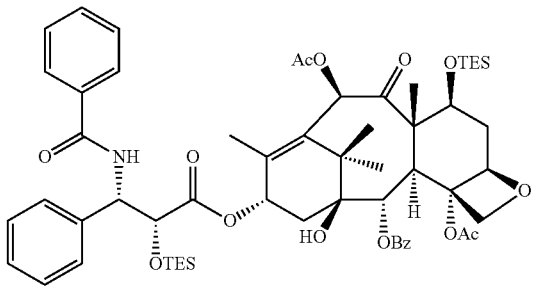

T3

Preparation of 1-hydroxy-7β-triethylsilyloxy-9-oxo-10β-acetyloxy-5β,20-epoxytax-11-ene-2α,4,13α-triyl 4-acetate 2-benzoate 13-[(2R,3S)-3-benzoylamino-2-trethylsilyloxy-3-phenylpropanoate] (T3) by the catalyst of KBr A solution of sodium hydride (60%, 5.6 eq, 320 mg) in 0.5 mL THF was cooled to −5~0° C. under nitrogen, and into which a solution of 7-TES-Baccatin III T2 (1 eq, 100 mg, LC purity 92%) in 1 mL THF was added dropwise. The reaction mixture was stirred at −5~0° C. for 0.5 hour, and then added a solution of (3R,4S)-1-benzoyl-4-phenyl-3-(triethylsilyl)oxy-2-azetidinone (β-lactam, 2 eq, 109 mg) and KBr (1 eq, 17 mg) in 0.5 mL THF dropwise. Then the reaction mixture was stirred at −5~7° C. for 2 hours until the reaction was completed. The reaction was neutralized with 2 mL 10% AcOH/THF at 0~5° C., and then diluted with 5 mL ethyl acetate and washed with 5 mL saturated sodium bicarbonate. The organic layer was dried by rotavapor to obtain the crude T3 (yield 75%, 154 mg, LC purity 69%).

Example 19

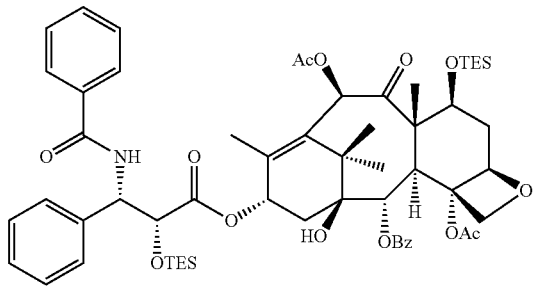

T3

Preparation of 1-hydroxy-7β-triethylsilyloxy-9-oxo-10β-acetyloxy-5β,20-epoxytax-11-ene-2α,4,13α-triyl 4-acetate 2-benzoate 13-[(2R,3S)-3-benzoylamino-2-trethylsilyloxy-3-phenylpropanoate] (T3) by the catalyst of MgBr$_2$ A solution of sodium hydride (60%, 5.6 eq, 320 mg) in 0.5 mL THF was cooled to −5~0° C. under nitrogen for 30 minutes, and into which a solution of 7-TES-Baccatin III (1 eq, 100 mg, LC purity 92%) in 1 mL THF was added slowly. The reaction mixture was stirred at −5~0° C. for 0.5 hour, and then was added a solution of (3R,4S)-1-benzoyl-4-phenyl-3-(triethylsilyl)oxy-2-azetidinone (β-lactam, 2 eq, 109 mg) and MgBr$_2$ (1 eq, 26 mg) in 0.5 mL THF dropwise. The reaction was stirred at −5~13° C. for 3 hours until the reaction was completed. The reaction was neutralized with 2 mL 10% AcOH/THF at 0~5° C. and then diluted with 5 mL ethyl acetate and washed with 5 mL saturated sodium bicarbonate. The organic layer was dried by rotavapor to obtain the crude T3 (yield 68%; 158 mg, LC purity 62%).

Example 20

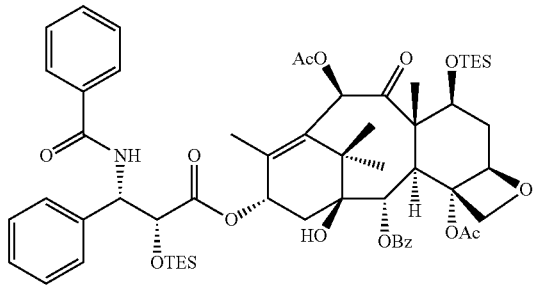

T3

Preparation of 1-hydroxy-7β-triethylsilyloxy-9-oxo-10β-acetyloxy-5β,20-epoxytax-11-ene-2α,4,13α-triyl 4-acetate 2-benzoate 13-[(2R,3S)-3-benzoylamino-2-trethylsilyloxy-3-phenylpropanoate] (T3) by the catalyst of LiBr A solution of sodium hydride (60%, 5.6 eq, 320 mg) in 0.5 mL THF was cooled to −5~0° C. under nitrogen for 30 minutes, and into which a solution of 7-TES-Baccatin III T2 (1 eq, 100 mg, LC purity 92%) in 1 mL THF was added slowly. The reaction mixture was stirred at −5~0° C. for 0.5 hour, and then was added a solution of (3R,4S)-1-Benzoyl-4-phenyl-3-(triethylsilyl)oxy-2-azetidinone (β-lactam, 2 eq, 109 mg) and LiBr (1 eq, 12 mg) in 0.5 mL THF dropwise. After the reaction mixture was stirred at 0~23° C. for 5 hours until the reaction was completed. The reaction was neutralized with 2 mL 10% AcOH/THF at 0~5° C. and then diluted with 5 mL ethyl acetate and washed with 5 mL saturated sodium bicarbonate. The organic layer was dried by rotavapor to obtain the crude T3 (yield 60%, 150 mg, LC purity 57%).

Example 21

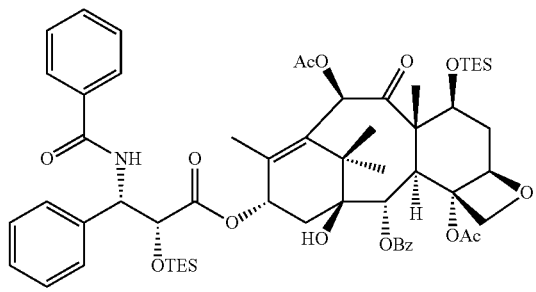

T3

Preparation of 1-hydroxy-7β-triethylsilyloxy-9-oxo-10β-acetyloxy-5β,20-epoxytax-11-ene-2α,4,13α-triyl 4-acetate 2-benzoate 13-[(2R,3S)-3-benzoylamino-2-trethylsilyloxy-3-phenylpropanoate] (T3) by the catalyst of ZnBr₂

A solution of sodium hydride (60%, 5.6 eq, 320 mg) in 0.5 mL THF was cooled to −5~0° C. under nitrogen for 30 minutes, and into which a solution of 7-TES-Baccatin III T2 (1 eq, 100 mg, LC purity 92%) in 1 mL THF was added slowly. The reaction mixture was stirred at −5~0° C. for 0.5 hour and then added a solution of (3R,4S)-1-Benzoyl-4-phenyl-3-(triethylsilyl)oxy-2-azetidinone (β-lactam, 2 eq, 109 mg) and ZnBr (1 eq, 35 mg) in 0.5 mL THF dropwise. The reaction mixture was stirred at 0~23° C. for 4 hours until the reaction was completed. The reaction was neutralized with 2 mL 10% AcOH/THF at 0~5° C., and then diluted with 5 mL ethyl acetate and washed with 5 mL saturated sodium bicarbonate. The organic layer was dried by rotavapor to obtain the crude T3 (LC purity 12%).

Example 22

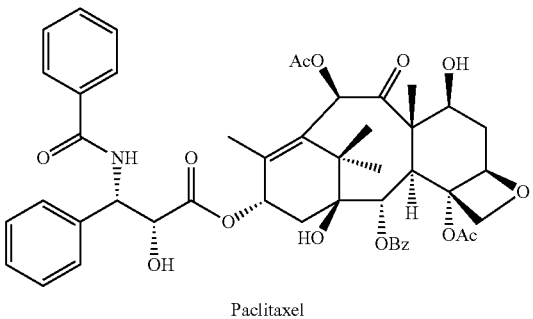

Paclitaxel

Preparation of (1S,2S,3R,4S,7R,9S,10S,12R,15S)-4,12-bis(acetyloxy)-1,9-dihydroxy-15-{[(2R,3S)-2-hydroxy-3-phenyl-3-(phenylformamido)propanoyl]oxy}-10,14,17,17-tetramethyl-11-oxo-6-oxatetracyclo[11.3.1.0$^{3,10}$.0$^{4,7}$]heptadec-13-en-2-yl benzoate (paclitaxel)

The crude T3 of EXAMPLE 14 in 22.5 mL MeOH was added 0.09 mL 32% HCl$_{(aq)}$ at −5~5° C. and then the reaction mixture was stirred for 3 hours. As the reaction temperature was raised to 20~30° C., the reaction mixture was stirred for 24 hours until the deprotection was completed. The reaction mixture was dried by rotavapor and then diluted with 40 mL CH₂Cl₂. After washed with 40 mL saturated sodium bicarbonate, the organic layer was dried by rotavapor to obtain the crude. The crude in 10 mL CH₂Cl₂ was slowly added 20 mL n-heptane to let paclitaxel precipitate. After filtration and dried the solid, 7.0 g paclitaxel (yield 90%, LC purity 95%) was obtained. $^1$H NMR (400 MHz, CDCl₃) δ 8.14 (d, J=7.2 Hz, 2H), 7.75 (d, J=7.2 Hz, 2H), 7.63-7.56 (m, 1H), 7.53-7.47 (m, 5H), 7.43-7.34 (m, 5H), 7.00 (d, J=8.8 Hz, 1H), 6.27 (s, 1H), 6.25 (dd, J=8.0 and 9.2 Hz, 1H), 5.80 (dd, J=2.8 and 9.2 Hz, 1H), 5.68 (d, J=7.2 Hz, 1H), 4.95 (dd, J=1.6 and 9.6 Hz, 1H), 4.80 (dd, J=2.8 and 5.2 Hz, 1H), 4.42-4.37 (m, 1H), 4.31 (d, J=8.4 Hz, 1H), 4.20 (d, J=8.4 Hz, 1H), 3.80 (d, J=7.2 Hz, 1H), 3.58 (d, J=5.2 Hz, 1H), 2.58-2.50 (m, 1H), 2.47 (d, J=4.0 Hz, 1H), 2.38 (s, 3H), 2.36-2.27 (m, 2H), 2.23 (s, 3H), 1.91-1.84 (m, 1H), 1.79 (s, 3H), 1.68 (s, 3H), 1.24 (s, 3H), 1.14 (s, 3H); $^{13}$C NMR (100 MHz, CDCl₃) δ 203.6, 172.7, 171.3, 170.3, 167.07 167.02, 142.0, 137.9, 133.7, 133.6, 133.1, 132.0, 130.2, 129.1, 129.0, 128.7, 128.4, 127.0, 84.4, 81.1, 79.0, 76.5, 75.5, 74.9, 73.2, 72.3, 72.2, 58.6, 55.0, 45.6 43.1 35.68, 35.62, 26.8, 22.6, 21.8, 20.8, 14.8, 9.5.

V. Synthesis of (2α,3α,4α,5β,7α,10β,13α)-4,10-bis(acetyloxy)-13-({(2R,3S)-3-[(tert-butoxycarbonyl)amino]-2-hydroxy-3-phenylpropanoyl}oxy)-1-hydroxy-9-oxo-5,20-epoxy-7,19-cyclotax-11-en-2-yl benzoate (L3) using Lewis acid catalysts (LiBr, CsBr, and KBr) (Examples 23-25)

Example 23

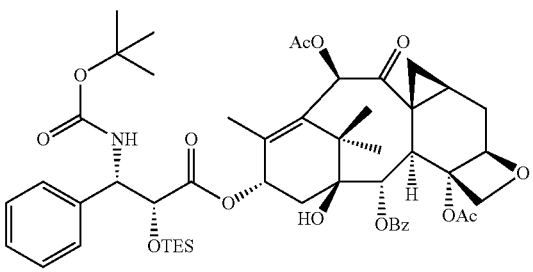

L3

Preparation of (2α,3α,4α,5β,7α,10β,13α)-4,10-bis(acetyloxy)-13-({(2R,3S)-3-[(tert-butoxycarbonyl)amino]-2-hydroxy-3-phenylpropanoyl}oxy)-1-hydroxy-9-oxo-5,20-epoxy-7,19-cyclotax-11-en-2-yl benzoate (L3) by the catalyst of LiBr A stirred solution of 10-deacetylbaccatin III (2 g, 3.4 mmol) in DCM (8 mL) and pyridine (7 mL) was cooled to −30° C., and added triflic anhydride (2.5 eq, 1.4 mL) over 20 minutes. The temperature of the reaction mixture was held below −15° C. during the addition and was kept at −20 to −25° C. for 30 min following the addition. After stirred 2 hours at 0° C., the reaction mixture was first diluted with $CH_2Cl_2$ and then washed successively with 1M $NaHSO_4$, sat'd $NaHCO_3$, and 50% sat'd NaCl. Each aqueous wash was back-extracted with DCM and the combined organic layers were dried ($MgSO_4$), filtered, and concentrated. The crude product was applied to a flash silica gel column. Evaporation of the fractions found by TLC to contain the product provided 7-O-triflate-baccatin III, L1 (yield 98%, 2.5 g). $^1$H NMR (400 MHz, $CDCl_3$) δ 8.09 (d, J=8 Hz, 1H), 7.61-7.65 (m, 1H), 7.48-7.52 (m, 2H), 6.63 (s, 1H), 5.67 (d, J=8 Hz, 1H), 5.50-5.55 (m, 1H), 4.94 (d, J=8 Hz, 1H), 4.83-4.86 (m, 1H), 4.34 (d, J=8 Hz, 1H), 4.14 (d, J=8 Hz, 1H), 4.02 (d, J=8 Hz, 1H), 2.83-2.91 (m, 1H), 2.31 (s, 3H), 2.25-2.29 (m, 2H), 2.23 (s, 3H), 2.21 (s, 3H), 2.11 (d, J=4 Hz, 1H), 1.87 (s, 3H), 1.24 (t, J=7 Hz, 3H), 1.2 (s, 3H), 1.05 (s, 3H); $^{13}$C NMR (100 MHz, $CDCl_3$) δ 200.6, 171.0, 168.8, 166.9, 149.5, 144.9, 133.8, 131.8, 130.8, 129.0, 128.7, 86.1, 83.0, 79.6, 78.6, 76.2, 75.9, 73.9, 67.7, 57.5, 47.3, 42.5, 38.1, 34.0, 26.4, 22.4, 20.7, 19.9, 14.8, 10.7.

A solution of 7-O-triflate-baccatin III L1 (2.5 g, 3.5 mmol) in dry ACN (40 mL) was treated with $NaN_3$ (2.7 g, 42 mmol). The mixture was refluxed under nitrogen for 5~6 hours. The mixture was diluted with EtOAc and wash with water and brine, dried over anhydrous magnesium sulfate, and evaporated. The product was purified by column chromatography. Evaporation of the fractions found by TLC to contain the product provided 7-deoxy-8-desmethyl-baccatin (III) L2 (yield 64%, 1.27 g). $^1$H NMR (400 MHz, $CDCl_3$) δ 8.13-8.15 (m, 1H), 7.60-7.64 (m, 1H), 7.47-7.51 (m, 2H), 6.35 (s, 1H), 5.62 (d, J=8 Hz, 1H), 4.85-4.79 (m, 1H), 4.74 (d, J=4 Hz, 1H), 4.30 (d, J=8 Hz, 1H), 4.17 (d, J=8 Hz, 1H), 4.03 (d, J=8 Hz, 1H), 2.45-2.50 (m, 1H), 2.35-2.40 (m, 1H), 2.29 (d, J=8 Hz, 1H), 2.27 (s, 3H), 2.23-2.26 (m, 1H), 2.21 (s, 3H), 2.07-2.11 (m, 1H), 2.05 (s, 3H), 1.79 (s, 1H), 1.63 (t, J=0.28 Hz, 1H), 1.35-1.29 (m, 1H), 1.22 (s, 3H), 1.10 (s, 3H); $^{13}$C NMR (100 MHz, $CDCl_3$) δ 202.1, 170.1, 169.7, 167.3, 144.1, 133.6, 132.7, 130.1, 129.4, 128.6, 84.8, 80.0, 79.3, 77.7, 76.2, 75.4, 67.6, 42.3, 38.8, 38.6, 31.7, 26.4, 26.0, 22.1, 20.9, 20.5, 15.4, 15.2.

A solution of sodium hydride (60%, 25 mg, 8 eq) in 1 mL THF was cooled to −15~−10° C. under nitrogen and then was added a solution of (2α,3α,4α,5β,7α,10β,13α)-4,10-bis(acetyloxy)-1,13-dihydroxy-9-oxo-5,20-epoxy-7,19-cyclotax-11-en-2-yl benzoate L2 (0.1 g, LC purity 73%) in 1 mL THF dropwise. The reaction mixture was stirred at −5~5° C. for 1 hour and then added a solution of (3R,4S)-tert-butyl 2-oxy-4-phenyl-3-(triethylsilyloxy)azetidine-1-carboxylate (β-lactam, 2 eq, 144 mg) in 0.4 mL THF dropwise. After stirred at −5~5° C. for 1 hour, the reaction mixture was added a solution of LiBr (6 mg) in 0.4 mL THF. The reaction mixture was stirred for another 3 hours until the reaction was completed. The reaction was neutralized with 0.5 mL 10% AcOH/THF at −5~5° C., and then diluted with 10 mL ethylacetate and washed with 8 mL saturated sodium bicarbonate. The organic layer was dried by rotavapor to obtain the crude L3 (LC purity 65%). $^1$H NMR (400 MHz, $CDCl_3$) δ 8.13 (d, J=8 Hz, 2H), 7.25-7.58 (m, 8H), 6.34 (s, 1H), 6.27-6.3 (m, 1H), 5.65 (d, J=8 Hz, 1H), 5.46 (d, J=12 Hz, 1H), 5.27 (d, J=8 Hz, 1H), 4.74 (d, J=4 Hz, 1H), 4.53 (s, 1H), 4.19 (d, J=8 Hz, 1H), 4.04 (d, J=8 Hz, 1H), 3.91 (d, J=8 Hz, 1H), 2.52 (s, 3H), 2.39-2.5 (m, 2H), 2.21-2.25 (m, 1H), 2.2 (s, 3H), 2.03-2.84 (m, 1H), 1.82 (s, 3H), 1.65-1.68 (m, 1H), 1.3-1.4 (m, 1H), 0.74-0.8 (m, 9H), 0.29-0.43 (m, 6H); $^{13}$C NMR (100 MHz, $CDCl_3$) δ 201.9, 171.3, 169.6, 167.4, 154.9, 140.9, 139.1, 133.59, 133.52, 130.2, 129.2, 128.5, 127.6, 126.3, 84.8, 81.6, 80.1, 79.7, 79.5, 79.4, 77.6, 75.6, 75.4, 70.9, 56.6, 42.9, 38.5, 35.9, 35.0, 32.2, 28.0, 26.0, 25.9, 22.3, 21.6, 20.8, 15.7, 14.5, 6.5, 4.2.

Example 24

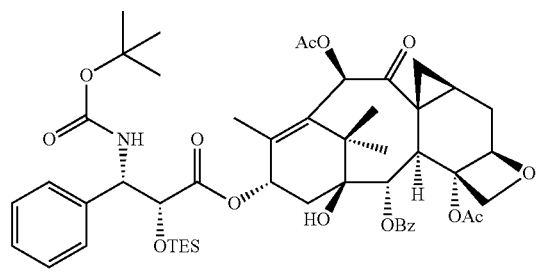

Preparation of (2α,3α,4α,5β,7α,10β,13α)-4,10-bis(acetyloxy)-13-({(2R,3S)-3-[(tert-butoxycarbonyl)amino]-2-hydroxy-3-phenylpropanoyl}oxy)-1-hydroxy-9-oxo-5,20-epoxy-7,19-cyclotax-11-en-2-yl benzoate (L3) by the catalyst of CsBr A solution of sodium hydride (60%, 25 mg, 8 eq) in 1 mL THF was cooled to −15~−10° C. under nitrogen and then added a solution of (2α,3α,4α,5β,7α,10β,13α)-4,10-bis(acetyloxy)-1,13-dihydroxy-9-oxo-5,20-epoxy-7,19-cyclotax-11-en-2-yl benzoate L2 (0.1 g, LC purity 73%) in 1 mL THF dropwise. The reaction mixture was stirred at −5~5° C. for 1 hour and then added a solution of (3R,4S)-tert-butyl 2-oxy-4-phenyl-3-(triethylsilyloxy)azetidine-1-carboxylate (β-lactam, 2 eq, 144 mg) in 0.4 mL THF dropwise. After stirred at −5~5° C. for 1 hour, the reaction mixture was added a solution of CsBr (6 mg) in 0.4 mL THF. The reaction mixture was stirred for 1.5 hours until the reaction was completed. The reaction was neutralized with 0.5 mL 10% AcOH/THF at −5~5° C. and then diluted with 10 mL ethylacetate and washed with 8 mL saturated sodium bicarbonate. The organic layer was dried by rotavapor to obtain the crude L3 (LC purity 75%).

Example 25

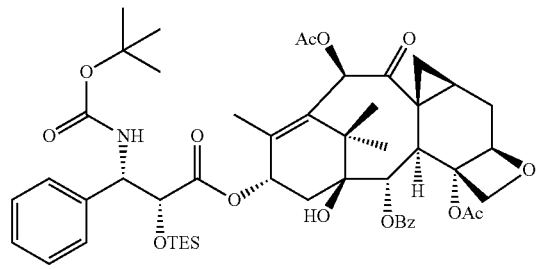

Preparation of (2α,3α,4α,5β,7α,10β,13α)-4,10-bis(acetyloxy)-13-({(2R,3S)-3-[(tert-butoxycarbonyl)amino]-2-hydroxy-3-phenylpropanoyl}oxy)-1-hydroxy-9-oxo-5,20-epoxy-7,19-cyclotax-11-en-2-yl benzoate (L3) by the catalyst of KBr A solution of sodium hydride (60%, 25 mg, 8 eq) in 1 mL THF was cooled to −15~−10° C. under nitrogen and then added a solution of (2α,3α,4α,5β,7α,10β,13α)-4,10-bis(acetyloxy)-1,13-dihydroxy-9-oxo-5,20-epoxy-7,19-cyclotax-11-en-2-yl benzoate L2 (0.1 g, LC purity 73%) in 1 mL THF slowly. The reaction mixture was stirred at −5~5° C. for 1 hour and then added a solution of (3R,4S)-tert-butyl 2-oxy-4-phenyl-3-(triethylsilyloxy)azetidine-1-carboxylate (β-lactam, 2 eq, 144 mg) in 0.4 mL THF dropwise. After stirred at −5~5° C. for 1 hour, the reaction mixture was added a solution of KBr (6 mg) in 0.4 mL THF. The reaction mixture was stirred for 1.5 hours until the reaction was completed. The reaction was neutralized with 0.5 mL 10% AcOH/THF at −5~5° C. and then diluted with 10 mL ethylacetate and washed with 8 mL saturated sodium bicarbonate. The organic layer was dried by rotavapor to obtain the crude L3 (LC purity 73%).

Example 26

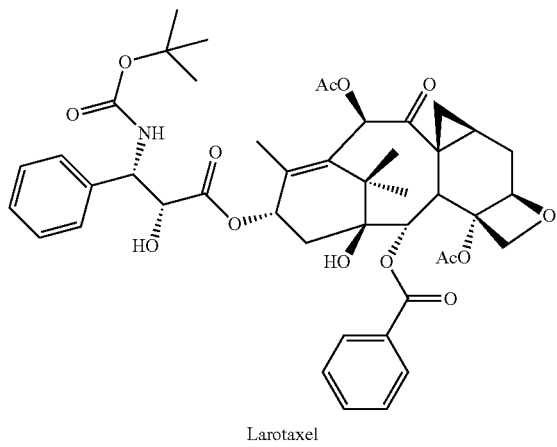

Larotaxel

Preparation of (1S,2S,3R,4S,7R,9S,11R,13R,16S)-4,13-bis(acetyloxy)-16-{[(2R,3S)-3-{[(tert-butoxy)carbonyl]amino}-2-hydroxy-3-phenylpropanoyl]oxy}-1-hydroxy-15,18,18-tri methyl-12-oxo-6-oxapentacyclo[12.3.1.0$^{3,11}$.0$^{4,7}$.0$^{9,11}$]octadec-14-en-2-yl benzoate (larotaxel)

Crude L3 (100 mg) dissolved in 4.5 mL MeOH was added 1.5 mL 0.5% HCl$_{(aq)}$ at 0~5° C. and then the reaction mixture was stirred for 2.5 hours at 0~5° C. Then the reaction was neutralized with 20 mL sat. NaHCO$_{3(aq)}$ under 0~5° C. The reaction mixture was dried by rotavapor and then diluted with 40 mL CH$_2$Cl$_2$. After washed with 40 mL saturated sodium bicarbonate, the organic layer was dried by rotavapor to obtain the crude product. The crude product in 5 mL CH$_2$Cl$_2$ was slowly added 10 mL n-heptane to precipitate larotaxel. After filtration the solid was dried to provide white solid larotaxel (yield 90%, 90 mg, LC purity 94%). $^1$H NMR (400 MHz, CDCl$_3$) δ 8.15 (d, J=7.6 Hz, 2H), 7.61 (t, J=6.4 Hz, 1H), 7.52 (t, J=8.0 Hz, 2H), 7.41-7.28 (m, 5H), 6.32 (s, 1H), 6.28-6.22 (m, 1H), 5.67 (d, J=7.6 Hz, 1H), 5.45 (d, J=9.6 Hz, 1H), 5.29 (d, J=7.6 Hz, 1H), 4.73 (d, J=3.2 Hz, 1H), 4.60 (s, 1H), 4.31 (d, J=8.4 Hz, 1H), 4.08 (dd, J=7.6, 10.0 Hz, 1H), 3.75 (bs, 1H), 2.38 (s, 3H), 2.54-2.18 (m, 2H), 2.20 (s, 3H), 1.84 (s, 3H), 1.67 (t, J=6.8 Hz, 1H), 1.27 (s, 9H), 1.256 (s, 3H), 1.250 (s, 3H), 0.93-0.83 (bs, 2H); $^{13}$C NMR (100 MHz, CDCl$_3$) δ 202.4, 173.4, 170.4, 170.3, 168.0, 141.1, 139.1, 134.5, 134.2, 130.9, 129.8, 129.4, 129.3, 128.6, 127.3, 85.4, 80.6, 80.1, 79.9, 76.3, 76.0, 74.4, 72.6, 68.6, 56.6, 43.5, 39.1, 36.4, 35.7, 32.7, 30.3, 28.8, 28.7, 26.8, 22.8, 22.1, 21.5, 16.2, 15.2.

VI. Synthesis of 7,10-di-methoxy-10-deacetylbaccatin (III) (C1) using Lewis acid catalysts (CsBr, CsBr/KBr, CsBr/MgBr$_2$, CsBr/ZnBr$_2$, and CsBr/CeCl$_3$) and sodium hydride (Examples 27-31)

Example 27

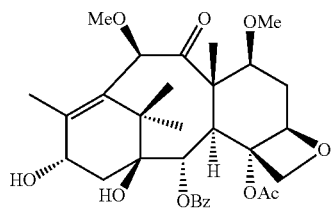

Preparation of 7,10-di-methoxy-10-deacetylbaccatin (III) (C1) catalyzed by CsBr A solution of sodium hydride (60%, 3 eq, 0.22 g) and CsBr (0.5 eq, 0.20 g) in co-solvent THF/DMF (2/1, 6 mL) was cooled to −20° C. under nitrogen and stirred for 20 min. 10-DAB (1 eq, 1 g)/Me$_2$SO$_4$ (10 eq, 1.74 mL) in THF/DMF (2/1, 6 mL) was added into the NaH/CsBr reaction mixture slowly. The reaction mixture was allowed to warm up to room temperature gradually and stirred for 2 hours until the reaction was completed. The reaction was quenched with 10% AcOH/THF, and extracted with CH$_2$Cl$_2$ and water. After partition, the organic layer was extracted with saturated NaHCO$_{3(aq)}$. The organic layer was concentrated and purified by recrystallization (CH$_2$Cl$_2$/Hexane) to provide C1 as a white solid (yield 50%, 0.37 g, LC purity 90%). $^1$H NMR (400 MHz, D$^6$-DMSO) δ 8.01 (d, J=7.2 Hz, 2H), 7.66 (t, J=7.4 Hz, 1H), 7.56 (t, J=7.6 Hz, 2H), 5.37 (d, J=7.2 Hz, 1H), 5.31 (d, J=4.0 Hz, 1H), 4.97 (d, J=8.4 Hz, 1H), 4.74 (s, 1H), 4.72-4.61 (m, 1H), 4.40 (s, 1H), 4.03 (dd, J=8.2, 13.4 Hz, 2H), 3.81 (dd, J=6.6, 10.6 Hz, 1H), 3.75 (d, J=7.2 Hz, 1H), 3.29 (s, 3H), 3.21 (s, 3H), 2.74-2.62 (m, 1H), 2.20 (s, 3H), 2.17 (d, J=8.4 Hz, 2H), 1.97 (s, 3H), 1.58-1.41 (m, 4H), 0.93 (s, 6H); $^{13}$C NMR (100 MHz, D$^6$-DMSO) δ 205.5, 169.7, 165.2, 144.1, 133.3, 132.8, 130.2, 129.5, 128.7, 83.3, 82.8, 80.5, 80.1, 76.9, 75.3, 74.4, 66.2, 56.7, 56.5, 56.1, 47.1, 42.5, 31.8, 26.9, 22.4, 20.5, 15.2, 10.1.

Example 28

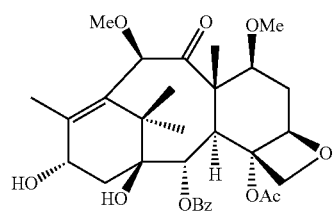

C1

Preparation of 7,10-di-methoxy-10-deacetylbaccatin (III) (C1) catalyzed by a mixture of CsBr and KBr A solution of sodium hydride (60%, 3 eq, 0.22 g)/CsBr (0.5 eq, 0.20 g)/KBr (0.1 eq, 0.02 g) in co-solvent THF/DMF (2/1, 6 mL) was cooled to −20° C. under nitrogen and stirred for 20 min. 10-DAB (1 eq, 1 g)/Me$_2$SO$_4$ (10 eq, 1.74 mL) in THF/DMF (2/1, 6 mL) was added into the NaH/CsBr/KBr solution slowly. The reaction mixture was allowed to warm up to room temperature gradually, and stirred for 2 hours until the reaction was completed. The reaction was quenched with 10% AcOH/THF, and extracted with CH$_2$Cl$_2$ and water. After partition, the organic layer was extracted with saturated NaHCO$_3$, concentrated and purified by recrystallization (CH$_2$Cl$_2$/Hexane) to provide C1 as a white solid (LC purity: 66%).

Example 29

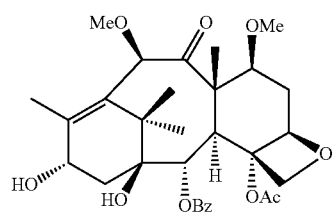

C1

Preparation of 7,10-di-methoxy-10-deacetylbaccatin (III) (C1) catalyzed by a mixture of CsBr and MgBr$_2$ A solution of sodium hydride (60%, 3 eq, 0.22 g)/CsBr (0.5 eq, 0.20 g)/MgBr$_2$ (0.1 eq, 0.03 g) in co-solvent THF/DMF (2/1, 6 mL) was cooled to −20° C. under nitrogen and stirred for 20 min. 10-DAB (1 eq, 1 g)/Me$_2$SO$_4$ (10 eq, 1.74 mL) in THF/DMF (2/1, 6 mL) was added into the NaH/CsBr/MgBr$_2$ mixture slowly. The reaction mixture was allowed to warm up to room temperature gradually and stirred for 2 hours until the reaction was completed. The reaction was quenched with 10% AcOH/THF, and extracted with CH$_2$Cl$_2$ and water. After partition, the organic layer was extracted with saturated NaHCO$_{3(aq)}$, concentrated and purified by recrystallization (CH$_2$Cl$_2$/Hexane) to provide C1 as a white solid. (LC purity 74%).

Example 30

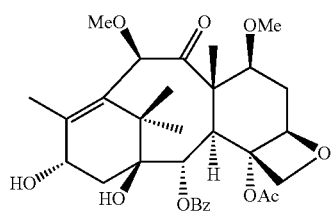

C1

Preparation of 7,10-di-methoxy-10-deacetylbaccatin (III) (C1) catalyzed by a mixture of CsBr and ZnBr$_2$ A solution of sodium hydride (60%, 3 eq, 0.22 g)/CsBr (0.5 eq, 0.20 g)/ZnBr$_2$ (0.1 eq, 0.04 g) in co-solvent THF/DMF (2/1, 6 mL) was cooled to −20° C. under nitrogen and stirred for 20 min. 10-DAB (1 eq, 1 g)/Me$_2$SO$_4$ (10 eq, 1.74 mL) in THF/DMF (2/1, 6 mL) was added into the NaH/CsBr/ZnBr$_2$ mixture slowly. The reaction mixture was allowed to warm up to room temperature gradually and stirred for 17 hours until the reaction was completed. The reaction was quenched with 10% AcOH/THF, and extracted with CH$_2$Cl$_2$ and water. After partition, the organic layer was extracted with saturated NaHCO$_{3(aq)}$, concentrated and purified by recrystallization (CH$_2$Cl$_2$/Hexane) to provide C1 as a white solid (LC purity 44%).

Example 31

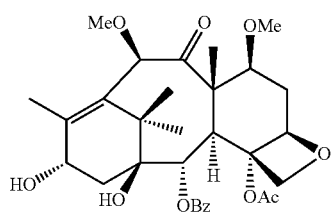

C1

Preparation of 7,10-di-methoxy-10-deacetylbaccatin (III) (C1) catalyzed by a mixture of CsBr and CeCl$_3$ A solution of sodium hydride (60%, 3 eq, 0.22 g)/CsBr (0.5 eq, 0.20 g)/CeCl$_3$ (0.1 eq, 0.05 g) in co-solvent THF/DMF (2/1, 6 mL) was cooled to −20° C. under nitrogen and stirred for 20 min. 10-DAB (1 eq, 1 g)/Me$_2$SO$_4$ (10 eq, 1.74 mL) in THF/DMF (2/1, 6 mL) was added into the NaH/CsBr/CeCl$_3$ mixture slowly. The reaction mixture was allowed to warm up to room temperature gradually and stirred for 2 hours until the reaction was completed. The reaction was quenched with 10% AcOH/THF, and extracted with CH$_2$Cl$_2$ and water. After partition, the organic layer was extracted with saturated NaHCO$_3{(aq)}$, concentrated and purified by recrystallization (CH$_2$Cl$_2$/Hexane) to provide C1 as a white solid (LC purity 61%).

VII. Synthesis of 7,10-di-methoxy-10-deacetylbaccatin (III) (C1) using Lewis acid catalysts (CsBr, and KBr) and (Naphthalene)⁻.Li⁺ (Examples 32-35)

Example 32

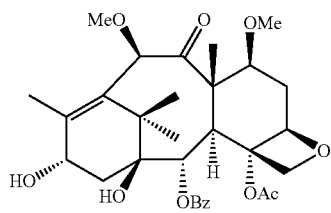

Preparation of 7,10-di-methoxy-10-deacetylbaccatin (III) (C1) by (Naphthalene)⁻.Li⁺ and catalyzed with CsBr Lithium (3.0 eq, 0.04 g) and naphthalene (3.3 eq, 0.78 g) in anhydrous THF (11 mL) was stirred under nitrogen at 25° C. for 16 hr, and then cooled to −78° C. A solution of 10-DAB (1 eq, 1 g) and Me$_2$SO$_4$ (10 eq, 1.74 mL) in anhydrous THF (9 mL) was added into the mixture of (Naphthalene)⁻.Li⁺ and CsBr (0.5 eq, 0.20 g) slowly. The reaction mixture was then allowed to return gradually to room temperature. After stirred for 6.5 h, the starting material was consumed. The reaction was quenched by 10% AcOH/THF and then extracted with CH$_2$Cl$_2$ and water. The organic layer was dried by rotavapor to provide crude C1 (HPLC purity: 22%).

Example 33

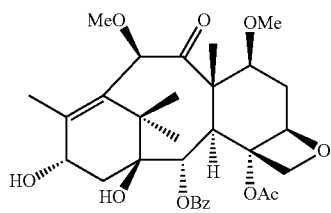

Preparation of 7,10-di-methoxy-10-deacetylbaccatin (III) (C1) by (Naphthalene)⁻.Li⁺ and catalyzed with CsBr under THF/DMF Lithium (3.0 eq, 0.04 g) and naphthalene (3.3 eq, 0.78 g) in anhydrous THF/DMF (10/1 mL) was stirred under nitrogen at 25° C. for 16 hr, and then cooled to −78° C. A solution of 10-DAB (1 eq, 1 g) and Me$_2$SO$_4$ (10 eq, 1.74 mL) in anhydrous THF/DMF (10/1 mL) was added into the mixture of (Naphthalene)⁻.Li⁺ and CsBr (0.5 eq, 0.20 g) slowly. The reaction mixture was then allowed to return gradually to room temperature. After stirred for 6.5 h, the starting material was consumed. The reaction was quenched by 10% AcOH/THF and then extracted with CH$_2$Cl$_2$ and water. The organic layer was dried by rotavapor to provide crude C1 (HPLC purity: 10%).

Example 34

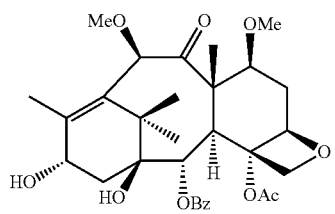

Preparation of 7,10-di-methoxy-10-deacetylbaccatin (III) (C1) by (Naphthalene)⁻.Li⁺ and catalyzed with KBr Lithium (3.0 eq, 0.04 g) and naphthalene (3.3 eq, 0.78 g) in anhydrous THF (11 mL) was stirred under nitrogen at 25° C. for 16 hr, and then cooled to −78° C. A solution of 10-DAB (1 eq, 1 g) and Me$_2$SO$_4$ (10 eq, 1.74 mL) in anhydrous THF (9 mL) was added into the mixture of (Naphthalene)-.Li⁺ and KBr (0.5 eq, 0.11 g) slowly. The reaction mixture was then allowed to return gradually to room temperature. After stirred for 6.5 h, the starting material was consumed. The reaction was quenched by 10% AcOH/THF and then extracted with CH$_2$Cl$_2$/water. The organic layer was dried by rotavapor to provide crude C1 (HPLC purity: 10%).

Example 35

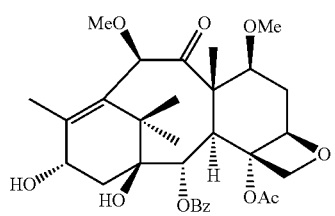

Preparation of 7,10-di-methoxy-10-deacetylbaccatin (III) (C1) by (Naphthalene)⁻.Li⁺ and catalyzed with KBr under THF/DMF Lithium (3.0 eq, 0.04 g) and naphthalene (3.3 eq, 0.78 g) in anhydrous THF/DMF (10/1 mL) was stirred under nitrogen at 25° C. for 16 hr, and then cooled to −78° C. A solution of 10-DAB (1 eq, 1 g) and Me$_2$SO$_4$ (10 eq, 1.74 mL) in anhydrous THF (10/1 mL) was added into the mixture of (Naphthalene)-.Li⁺ and KBr (0.5 eq, 0.11 g) slowly. The reaction mixture was then allowed to return gradually to room temperature. After stirred for 6.5 h, the starting material was consumed. The reaction was quenched by 10% AcOH/THF and then extracted with CH$_2$Cl$_2$/water. The organic layer was dried by rotavapor to provide crude C1 (HPLC purity: 9%).

VIII. Synthesis of 1-hydroxy-7β,10β-di-methoxy-9-oxo-5β,20-epoxytax-11-ene-2α,4,13α-triyl 4-acetate 2-benzoate 13-{(2R,3S)-3-[(tert-butoxycarbonyl)amino]-2-trethylsilyloxy-3-phenylpropanoate} (C2) using Lewis acid catalysts (LiBr, MgBr$_2$, CsBr, CeCl$_3$, KBr, and FeCl$_3$) (Examples 36-41)

Example 36

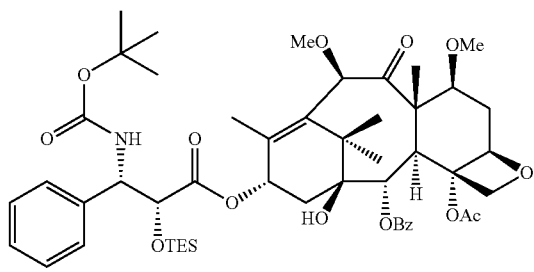

C2

Preparation of 1-hydroxy-7β,10β-di-methoxy-9-oxo-5β,20-epoxytax-11-ene-2α,4,13α-triyl 4-acetate 2-benzoate 13-{(2R,3S)-3-[(tert-butoxycarbonyl)amino]-2-trethylsilyloxy-3-phenylpropanoate} (C2) by the catalyst of LiBr A solution of sodium hydride (60%, 8 eq, 112 mg) in 2 mL THF was cooled to –15° C. under nitrogen. 7,10-di-methoxy-10-DAB C1 (1 eq, 200 mg) dissolved in 2 mL THF was added to the sodium hydride solution. The reaction mixture was added a mixture of (3R,4S)-tert-butyl 2-oxy-4-phenyl-3-(triethylsilyloxy)azetidine-1-carboxylate (β-lactam, 2.5 eq, 329 mg) and LiBr (0.5 eq, 15 mg) in 2 mL THF slowly. The reaction mixture was stirred for 2 hours at –15° C. to 20° C. until the reaction was completed. The reaction was quenched with 10% AcOH/THF, and extracted with ethylacetate and water. The organic layer was dried by rotavapor to obtain crude C2 (LC purity 58%). $^1$H NMR (400 MHz, CDCl$_3$) δ 8.10 (d, J=7.2 Hz, 2H), 7.58 (t, J=7.4 Hz, 1H), 7.47 (t, J=7.6 Hz, 2H), 7.37 (t, J=7.4 Hz, 2H), 7.32-7.27 (m, 3H), 6.29 (t, J=8.6 Hz, 1H), 5.65 (d, J=7.2 Hz, 1H), 5.49 (d, J=9.6 Hz, 1H), 5.27 (d, J=10.0 Hz, 1H), 5.00 (d, J=7.6 Hz, 1H), 4.80 (s, 1H), 4.55 (s, 1H), 4.25 (dd, J=8.4, 52.0 Hz, 2H), 3.94-3.83 (m, 2H), 3.45 (s, 3H), 3.30 (s, 3H), 2.76-2.65 (m, 1H), 2.53 (s, 3H), 2.41-2.14 (m, 2H), 1.95 (s, 3H), 1.85-1.74 (m, 2H), 1.72 (s, 3H), 1.68 (s, 1H), 1.33 (s, 9H), 1.24 (s, 3H), 1.20 (s, 3H), 0.78 (t, J=7.8 Hz, 9H), 0.49-0.28 (m, 6H); $^{13}$C NMR (100 MHz, CDCl$_3$) δ 204.9, 171.7, 170.0, 166.9, 155.2, 139.4, 138.9, 135.0, 133.5, 130.1, 129.2, 128.6, 128.5, 127.7, 126.4, 84.1, 82.4, 81.5, 80.6, 79.8, 78.9, 76.4, 75.2, 74.8, 71.6, 57.2, 57.0, 56.7, 47.2, 43.3, 35.2, 31.9, 28.1, 26.6, 22.9, 21.2, 14.3, 10.3, 6.5, 4.2.

Example 37

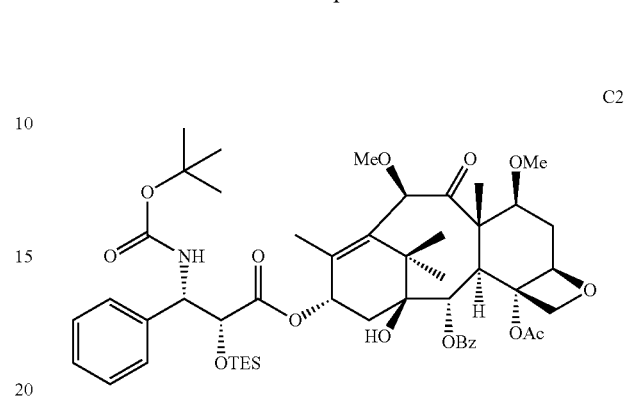

C2

Preparation of 1-hydroxy-7β,10β-di-methoxy-9-oxo-5β,20-epoxytax-11-ene-2α,4,13α-triyl 4-acetate 2-benzoate 13-{(2R,3S)-3-[(tert-butoxycarbonyl)amino]-2-trethylsilyloxy-3-phenylpropanoate} (C2) by the catalyst of MgBr$_2$ A solution of sodium hydride (60%, 8 eq, 112 mg) in 2 mL THF was cooled to –15° C. under nitrogen. 7,10-di-methoxy-10-DAB (1 eq, 200 mg) dissolved in 2 mL THF was added into the NaH solution. Then the reaction mixture was added a mixture of (3R,4S)-tert-butyl 2-oxy-4-phenyl-3-(triethylsilyloxy)azetidine-1-carboxylate (β-lactam, 2.5 eq, 329 mg) and MgBr$_2$ (0.5 eq, 32.2 mg) in 2 mL THF slowly. The reaction mixture was stirred for 2 hours at –15~20° C. until the reaction was completed. The reaction was quenched with 10% AcOH/THF, and extracted with ethylacetate and water. The organic layer was dried by rotavapor to obtain crude C2 (LC purity 79%).

Example 38

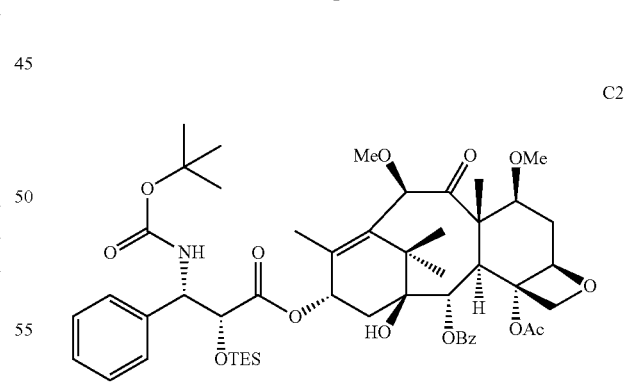

C2

Preparation of 1-hydroxy-7β,10β-di-methoxy-9-oxo-5β,20-epoxytax-11-ene-2α,4,13α-triyl 4-acetate 2-benzoate 13-{(2R,3S)-3-[(tert-butoxycarbonyl)amino]-2-trethylsilyloxy-3-phenylpropanoate} (C2) by the catalyst of CsBr A solution of sodium hydride (60%, 8 eq, 112 mg) in 2 mL THF was cooled to –15° C. under nitrogen. 7,10-di-methoxy- 10-DAB (1 eq, 200 mg) in 2 mL THF was added to the NaH solution. The reaction mixture was added a mixture of (3R, 4S)-tert-butyl 2-oxy-4-phenyl-3-(triethylsilyloxy)azetidine-1-carboxylate (β-lactam, 2.5 eq, 329 mg) and CsBr (0.5 eq, 37.2 mg) in 2 mL THF slowly. The reaction mixture was stirred for 1.5 hours at −15~20° C. until the reaction was completed. The reaction was quenched with 10% AcOH/THF, and extracted with ethylacetate and water. The organic layer was dried by rotavapor to obtain crude C2 (LC purity 85%).

Example 39

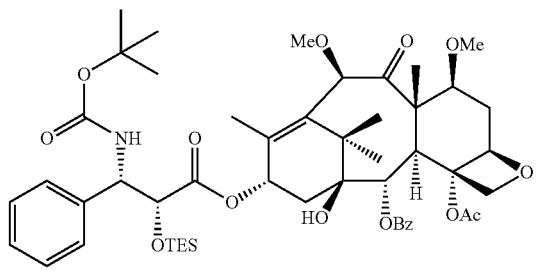

C2

Preparation of 1-hydroxy-7β,10β-di-methoxy-9-oxo-5β,20-epoxytax-11-ene-2α,4,13α-triyl 4-acetate 2-benzoate 13-{(2R,3S)-3-[(tert-butoxycarbonyl)amino]-2-trethylsilyloxy-3-phenylpropanoate} (C2) by the catalyst of CeCl₃

A solution of sodium hydride (60%, 8 eq, 112 mg) in 2 mL THF was cooled to −15° C. under nitrogen. 7,10-di-methoxy-10-DAB (1 eq, 200 mg) in 2 mL THF was added to the NaH solution. The reaction mixture was added a mixture of (3R, 4S)-tert-butyl 2-oxy-4-phenyl-3-(triethylsilyloxy)azetidine-1-carboxylate (β-lactam, 2.5 eq, 329 mg) and CeCl₃ (0.5 eq, 43.0 mg) in 2 mL THF slowly. The reaction mixture was stirred for 2.5 hours at −15~20° C. until the reaction was completed. The reaction was quenched with 10% AcOH/THF, and extracted with ethylacetate and water. The organic layer was dried by rotavapor to obtain crude C2 (LC purity 87%).

Example 40

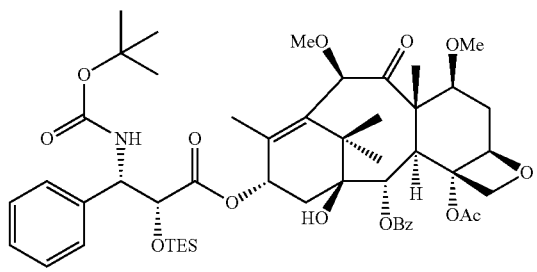

C2

Preparation of 1-hydroxy-7β,10β-di-methoxy-9-oxo-5β,20-epoxytax-11-ene-2α,4,13α-triyl 4-acetate 2-benzoate 13-{(2R,3S)-3-[(tert-butoxycarbonyl)amino]-2-trethylsilyloxy-3-phenylpropanoate} (C2) by the catalyst of KBr A solution of sodium hydride (60%, 8 eq, 112 mg) in 2 mL THF was cooled to −5° C. under nitrogen. 7,10-di-methoxy-10-DAB (1 eq, 200 mg) in 2 mL THF was added dropwise to the NaH solution. The reaction mixture was added a mixture of (3R,4S)-tert-butyl 2-oxy-4-phenyl-3-(triethylsilyloxy)azetidine-1-carboxylate (β-lactam, 2.5 eq, 329 mg) and KBr (0.5 eq, 20 mg) in 2 mL THF slowly. The reaction mixture was stirred for 2.5 hours at −15~20° C. until the reaction was completed. The reaction was quenched with 10% AcOH/THF, and extracted with ethylacetate and water. The organic layer was dried by rotavapor to obtain crude C2 (LC purity 72%).

Example 41

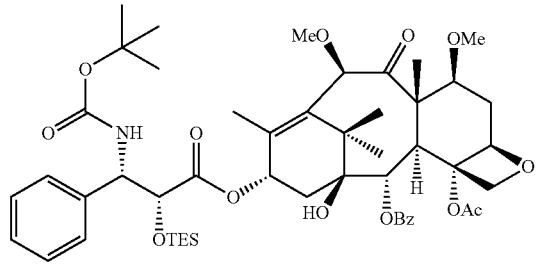

C2

Preparation of 1-hydroxy-7β,10β-di-methoxy-9-oxo-5β,20-epoxytax-11-ene-2α,4,13α-triyl 4-acetate 2-benzoate 13-{(2R,3S)-3-[(tert-butoxycarbonyl)amino]-2-trethylsilyloxy-3-phenylpropanoate} (C2) by the catalyst of FeCl₃

A solution of sodium hydride (60%, 8 eq, 112 mg) in 2 mL THF was cooled to −5° C. under nitrogen. 7,10-di-methoxy-10-DAB (1 eq, 200 mg) in 2 mL THF was added dropwise to the NaH solution. The reaction mixture was added a mixture of (3R,4S)-tert-butyl 2-oxy-4-phenyl-3-(triethylsilyloxy)azetidine-1-carboxylate (β-lactam, 2.5 eq, 329 mg) and FeCl₃ (0.5 eq, 28.4 mg) in 2 mL THF. The reaction mixture was stirred for 2.5 hours at −15~20° C. until the reaction was completed. The reaction was quenched with 10% AcOH/THF, and extracted with ethylacetate and water. The organic layer was dried by rotavapor to obtain crude C2 (yields 45%, LC purity 95%).

Example 42

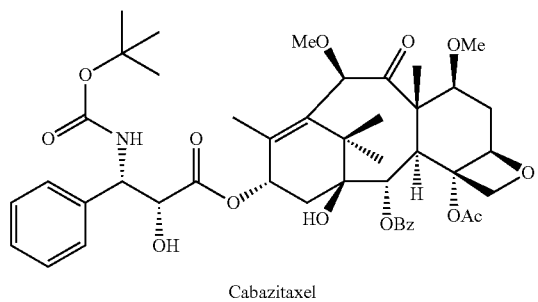

Cabazitaxel

Preparation of (1S,2S,3R,4S,7R,9S,10S,12R,15S)-4-(acetyloxy)-15-{[(2R,3S)-3-{[(tert-butoxy)carbonyl]amino}-2-hydroxy-3-phenylpropanoyl]oxy}-1,9,12-trihydroxy-10,14,17,17-tetramethyl-11-oxo-6-oxatetracyclo[11.3.1.0$^{3,10}$.0$^{4,7}$]heptadec-13-en-2-yl benzoate (cabazitaxel)

32% HCl$_{(aq)}$ was added dropwise to a solution of C3 (490 mg, 1 eq) in 3.5 mL MeOH at −5~5° C., until the pH reached between 1~2. The reaction mixture was stirred at −5~5° C. until the deprotection was completed, then it was quenched with saturated NaHCO$_{3(aq)}$ and extracted with CH$_2$Cl$_2$. The organic layer was concentrated and purified by recrystallization (CH$_2$Cl$_2$/Hexane) to provide cabazitaxel as a white solid (yield 65%, 280 mg; LC purity 98%). $^1$H NMR (400 MHz, CDCl$_3$) δ 8.09 (d, J=7.6 Hz, 2H), 7.60 (t, J=7.4 Hz, 1H), 7.48 (t, J=8.0 Hz, 2H), 7.42-7.36 (m, 4H), 7.36-7.29 (m, 1H), 6.20 (t, J=8.6 Hz, 1H), 5.63 (d, J=7.2 Hz, 1H), 5.43 (d, J=9.6 Hz, 1H), 5.26 (d, J=8.8 Hz, 1H), 4.97 (d, J=8.0 Hz, 1H), 4.79 (s, 1H), 4.62 (s, 1H), 4.23 (dd, J=8.2, 50.0 Hz, 2H), 3.90-3.77 (m, 2H), 3.50-3.40 (m, 4H), 3.30 (s, 3H), 2.75-2.64 (m, 1H), 2.36 (s, 3H), 2.32-2.18 (m, 2H), 1.88 (s, 3H), 1.84-1.74 (m, 2H), 1.71 (s, 3H), 1.67 (s, 1H), 1.36 (s, 9H), 1.23-1.17 (m, 6H); $^{13}$C NMR (100 MHz, CDCl$_3$) δ 204.9, 172.6, 170.3, 166.8, 155.3, 138.7, 138.3, 135.4, 133.6, 130.1, 129.1, 128.7, 128.6, 127.9, 126.7, 84.0, 82.5, 81.6, 80.7, 80.1, 78.6, 76.4, 74.5, 73.7, 72.4, 57.2, 57.0, 56.8, 47.3, 43.2, 35.2, 32.0, 28.1, 26.7, 22.6, 20.6, 14.5, 10.3.

Example 43

The following Table 1 summarizes the examples 1 to 42.

TABLE 1

Summary of Examples 1-42

| Example No. | Reaction | Base | Lewis Acid Catalyst | T(° C.)/t(hr) | Solution | LC purity (%) | % yield |
|---|---|---|---|---|---|---|---|
| 1. | D2 (7,10-TES-10-DAB) (one-pot-disilylation of 10-DAB) | triethylamine/DMAP | LiBr | 1. 65~70/3~5 2. 20~30/13~16 | THF | 98 | 89 |
| 2. | D2 (silylation of 7-TES-10-DAB) | triethylamine/DMAP | MgBr$_2$ | reflux/46.5 | THF | 48 | —* |
| 3. | D2 (silylation of 7-TES-10-DAB) | triethylamine/DMAP | LiBr and CsBr | reflux/46.5 | THF | 78 | —* |
| 4. | D2 (silylation of 7-TES-10-DAB) | triethylamine/DMAP | LiBr and ZnBr$_2$ | reflux/46.5 | THF | 58 | —* |
| 5. | D2 (silylation of 7-TES-10-DAB) | triethylamine/DMAP | LiBr and CuBr | reflux/46.5 | THF | 26 | —* |
| 6. | D3 (coupling at C-13) | NaH | LiBr | −5~5/3 | THF | 96 | —* |
| 7. | D3 (coupling at C-13) | NaH | CsBr | −5~5/3 | THF | 94 | —* |
| 8. | D3 (coupling at C-13) | NaH | MgBr$_2$ | −5~5/3 | THF | 43 | —* |
| 9. | D3 (coupling at C-13) | NaH | CeCl$_3$ | −5~5/3 | THF | 26 | —* |
| 10. | Docetaxel (deprotection) | | | | | 96 | 60 |
| 11. | T1 (C10-acetylation of 10-DAB) | | ZnBr$_2$ | 60/19 | THF | 95 | 73 |
| 12. | T1 (C10-acetylation of 10-DAB) | | LiBr | 60/17 | THF | 65 | 50 |
| 13. | T1 (C10-acetylation of 10-DAB) | | ZnCl$_2$ | 60/17 | THF | 83 | 74 |
| 14. | T1 (C10-acetylation of 10-DAB) | | CuBr | 60/21.5 | THF | 89 | 60 |
| 15. | T1 (C10-acetylation of 10-DAB) | | CuBr and LiBr | 60/21.5 | THF | 91 | —* |
| 16. | T1 (C10-acetylation of 10-DAB) | | CuBr and ZnBr$_2$ | 60/21.5 | THF | 97 | 75 |
| 17. | T3 (coupling at C-13) | NaH | CsBr | −5~0/0.5; 0~7/2 | THF | 69 | 75 |
| 18. | T3 (coupling at C-13) | NaH | KBr | −5~0/0.5; −5~7/2 | THF | 69 | 75 |
| 19. | T3 (coupling at C-13) | NaH | MgBr$_2$ | −5~0/0.5; −5~13/3 | THF | 62 | 67 |
| 20. | T3 (coupling at C-13) | NaH | LiBr | −5~0/0.5; 0~23/5 | THF | 57 | 60 |
| 21. | T3 (coupling at C-13) | NaH | ZnBr$_2$ | −5~0/0.5; 0~23/5 | THF | 12 | —* |
| 22. | Paclitaxel (deprotection) | | | | | 95% | 90%, |
| 23. | L3 (coupling at C-13) | NaH | LiBr | −5~5/3 | THF | 65 | —* |
| 24. | L3 (coupling at C-13) | NaH | CsBr | −5~5/1.5 | THF | 75 | —* |
| 25. | L3 (coupling at C-13) | NaH | KBr | −5~5/1.5 | THF | 73 | —* |
| 26. | Larotaxel | | | | | 94 | 90 |
| 27. | C1(C7,C10-dimethylation of 10-DAB) | NaH | CsBr | −20/2 | THF/DMF | 90 | 50 |

TABLE 1-continued

Summary of Examples 1-42

| Example No. | Reaction | Base | Lewis Acid Catalyst | T(° C.)/t(hr) | Solution | LC purity (%) | % yield |
|---|---|---|---|---|---|---|---|
| 28. | C1(C7,C10-dimethylation of 10-DAB) | NaH | CsBr & KBr | −20~RT/2 | THF/DMF | 66 | —* |
| 29. | C1(C7,C10-dimethylation of 10-DAB) | NaH | MgBr$_2$ & CsBr | −20~RT/2 | THF/DMF | 74 | —* |
| 30. | C1(C7,C10-dimethylation of 10-DAB) | NaH | ZnBr$_2$ & CsBr | −20~RT/17 | THF/DMF | 44 | —* |
| 31. | C1(C7,C10-dimethylation of 10-DAB) | NaH | CeCl$_3$ & CsBr | −20~RT/2 | THF/DMF | 61 | —* |
| 32. | C1(C7,C10-dimethylation of 10-DAB) | (Naphthalene)$^-$•Li$^+$ | CsBr | RT/6.5 | THF | 22 | —* |
| 33. | C1(C7,C10-dimethylation of 10-DAB) | (Naphthalene)$^-$•Li$^+$ | CsBr | RT/6.5 | THF/DMF; 10/1 | 10 | —* |
| 34. | C1(C7,C10-dimethylation of 10-DAB) | (Naphthalene)$^-$•Li$^+$ | KBr | RT/6.5 | THF | 10 | —* |
| 35. | C1(C7,C10-dimethylation of 10-DAB) | (Naphthalene)$^-$•Li$^+$ | KBr | RT/6.5 | THF/DMF; 10/1 | 9 | —* |
| 36. | C2 | NaH | LiBr | −15~20/2 | THF | 58 | —* |
| 37. | C2 | NaH | MgBr$_2$ | −15~20/2 | THF | 79 | —* |
| 38. | C2 | NaH | CsBr | −15~20/1.5 | THF | 85 | —* |
| 39. | C2 | NaH | CeCl$_3$ | −15~20/2.5 | THF | 87 | —* |
| 40. | C2 | NaH | KBr | −5~5/2.5 | THF | 72 | —* |
| 41. | C2 | NaH | FeCl$_3$ | −5~5/2.5 | THF | 95 | 45 |
| 42. | Cabazitaxel (Deprotection) | | | | | 98 | 65 |

*"—" means not determined.

The invention, and the manner and process of making and using it, are now described in such full, clear, concise and exact terms as to enable any person skilled in the art to which it pertains, to make and use the same. It is to be understood that the foregoing describes preferred embodiments of the present disclosure and that modifications may be made therein without departing from the scope of the present disclosure as set forth in the claims. To particularly point out and distinctly claim the subject matter regarded as invention, the following claims conclude the specification

We claim:

1. A process for preparing a taxoid of general formula (X),

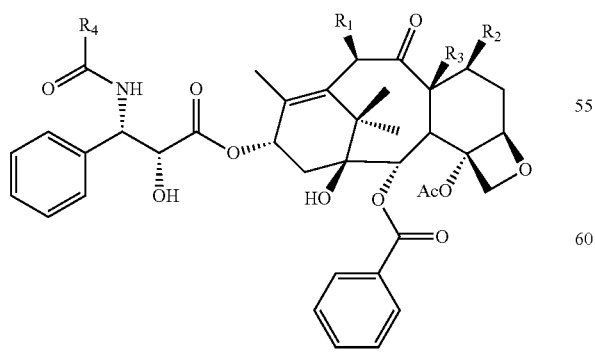

comprising the steps of:

(a) reacting a protected baccatin III derivative (B)

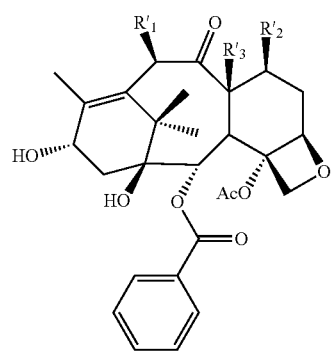

with a β-lactam of the general formula (C)

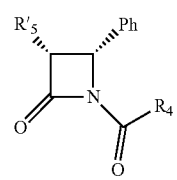

in the presence of one or more Lewis acids ML and a first base agent to obtain a protected taxoid of general formula (X°) having one or more silyl ether protecting groups;

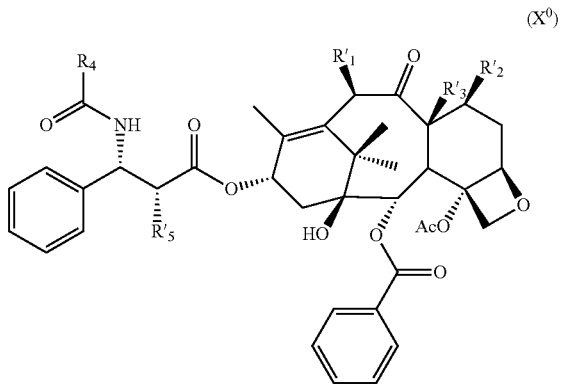

and
(b) removing the silyl ether protecting groups to obtain the taxoid of general formula (X);
wherein:
M is selected from the group consisting of cations of Li, Na, K, Rb, Cs, Be, Mg, Ca, Sr, Ba, Cu, Ag, Au, Zn, Cd, Hg, Fe, Co, Ni, Ru, Rh, Pd, Os, Ir, Pt, Sc, Y, Ti, V, Nb, Co, B, Al, In, Sn, Ce, and any combination thereof;
L is a counter ion to M;
$R'_1$ is alkoxy, —O—C(=O)—$R_{10}$, or —O—Si($R_{11}$)($R_{12}$)($R_{13}$);
$R'_2$ is alkoxy, or —O—Si($R_{21}$)($R_{22}$)($R_{23}$), or $R'_2$ is H when $R'_3$ is taken together with C7 to form a cycloalkyl ring;
$R'_3$ is alkyl, or taken together with C7 to form a cycloalkyl ring;
$R'_5$ is —O—Si($R_{51}$)($R_{52}$)($R_{53}$);
$R_1$ is hydroxyl, alkoxy, or —O—C(=O)—$R_{10}$;
$R_2$ is hydroxyl, alkoxy, or $R_2$ is H when $R_3$ is taken together with C7 to form a cycloalkyl ring;
$R_3$ is alkyl, or taken together with C7 to form a cycloalkyl ring;
$R_4$ is alkoxy or phenyl;
$R_{10}$ is alkyl; and
$R_{11}$, $R_{12}$, $R_{13}$, $R_{21}$, $R_{22}$, $R_{23}$, $R_{51}$, $R_{52}$, and $R_{53}$ are independently alkyl.

2. The process of claim 1, wherein M is selected from the group consisting of metal cations of Li, K, Cs, Mg, Sc, Ti, V, Cu, Zn, B, Al, In, Sn, Ce, and any combination thereof.

3. The process of claim 1, wherein L is selected from the group consisting of oxide, acid radical, halide anion, Br⁻, Cl⁻, F⁻, I⁻, $CO_3^{2-}$, $O^{2-}$, $ClO_4^-$, $(OCH(CH_3)_2)^-$, triflate, and any combination thereof.

4. The process of claim 1, wherein ML is LiBr, $MgBr_2$, CsBr, $ZnBr_2$, $ZnCl_2$, CuBr, $Cu(CF_3SO_4)_2$, $BF_3.OEt_2$, KBr, $TiCl_4$, $SnCl_2$, $ScCl_3$, $VCl_3$, $AlCl_3$, $InCl_3$, $Al_2CO_3$, $CeCl_3$, $Ag_2O$, $ZnClO_4$, $LiClO_4$, $Ti\{OCH(CH_3)_2\}_4$ or any combination thereof.

5. The process of claim 1, wherein $R'_1$ and $R'_2$ are alkoxyl groups, or $R'_1$ is —O—Si($R_{11}$)($R_{12}$)($R_{13}$) and $R'_2$ is —O—Si($R_{21}$)($R_{22}$)($R_{23}$).

6. The process of claim 1, wherein $R_4$ is —OC($CH_3$)$_3$.

7. The process of claim 1, wherein $R'_5$ is —O—Si($CH_2CH_3$)$_3$ or —O—Si($CH_3$)$_3$.

8. The process of claim 1, wherein $R'_1$ is O—Si($R_{11}$)($R_{12}$)($R_{13}$);
$R'_2$ is —O—Si($R_{21}$)($R_{22}$)($R_{23}$);
$R'_3$ is alkyl;
$R'_5$ is —O—Si($CH_2CH_3$)$_3$;
$R_1$ is hydroxyl;
$R_2$ is hydroxyl; and
the protected groups are removed by reacting the protected taxoid with an acid.

9. The process of claim 1, wherein the first base agent is an amine, or a metal hydride.

10. The process of claim 9, wherein the first base agent is pyridine, triethylamine, 2,2-tert-butyl-pyridine, 2,6-tert-butyl-4-methyl-pyridine, N,N,N',N'-tetramethyl-naphthalene-1,8-diamine, N-1-Naphthylethylenediamine, sodium hydride, or potassium hydride.

11. The process of claim 1, wherein the β-lactam is (3R,4S)-tert-butyl-2-oxy-4-phenyl-3-(triethylsilyloxy)azetidine-1-carboxylate, or (3R,4S)-phenyl-2-oxy-4-phenyl-3-(triethylsilyloxy)azetidine-1-carboxylate.

12. The process of claim 1, wherein the taxoid is paclitaxel, docetaxel, larotaxel, or cabazitaxel.

13. The process for claim 1, further comprising the step of:
A) reacting one or more Lewis acid M'L' and optionally a second base agent with a baccatin III derivative (A)

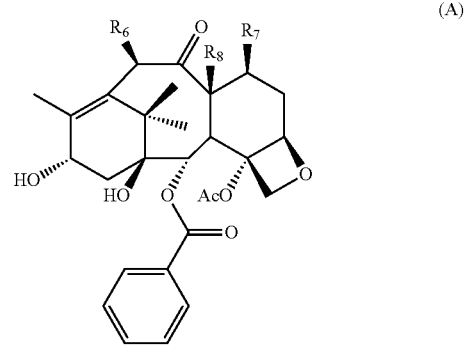

to form the protected baccatin III derivative (B) of claim 1,

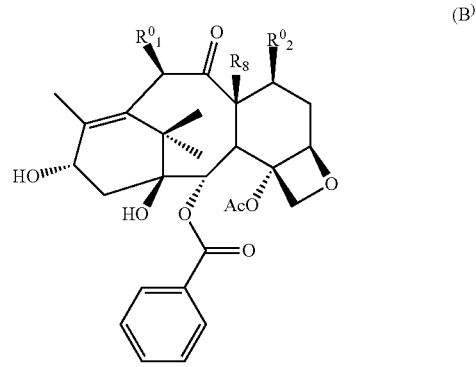

wherein:
M' is selected from the group consisting of cations of Li, Na, K, Rb, Cs, Be, Mg, Ca, Sr, Ba, Cu, Ag, Au, Zn, Cd, Hg, Fe, Co, Ni, Ru, Rh, Pd, Os, Ir, Pt, Sc, Y, Ti, V, Nb, Co, B, Al, In, Sn, Ce, and any combination thereof;
L' is a counter ion of M';
$R_6$ is hydroxyl, alkoxy, or —O—C(=O)—$R_{60}$;
$R_7$ is hydroxyl, alkoxy, —O—C(=O)—$R_{70}$, or —O—Si($R_{71}$)($R_{72}$)($R_{73}$);
$R_8$ is alkyl;
$R_{60}$, and $R_{70}$ are independently alkyl; and
$R_{71}$, $R_{72}$, and $R_{73}$, are independently alkyl.

14. The process of claim 13, wherein:
R'$_1$ is alkoxy;
R'$_2$ is alkoxy; and
R$_6$ and R$_7$ are both alkoxy.

15. The process of claim 14, wherein R'$_1$ and R'$_2$ are both methoxy, and R$_8$ is methyl.

16. The process of claim 13, wherein:
R'$_1$ is —O—Si(R$_{11}$)(R$_{12}$)(R$_{13}$);
R'$_2$ is —O—Si(R$_{21}$)(R$_{22}$)(R$_{23}$);
R$_6$ is hydroxyl; and
R$_7$ is —O—Si(R$_{71}$)(R$_{72}$)(R$_{73}$).

17. The process of claim 16, further comprising the step of:
A') reacting 10-DAB with a silylation reagent to obtain the baccatin derivative (A) of claim 13; and

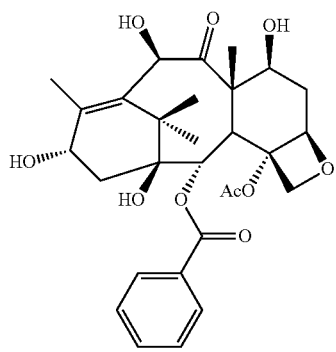

10-DAB optionally the step A') herein and the step A) of claim 13 are performed in the same reaction pot.

18. The process of claim 17, wherein R$_{11}$, R$_{12}$, R$_{13}$, R$_{21}$, R$_{22}$, R$_{23}$, R$_{71}$, R$_{72}$, and R$_{73}$ are independently —CH$_2$CH$_3$ or —CH$_3$.

19. The process of claim 13, wherein the first base agent and the second base agent are independently an amine base, a metal hydride, or a coordination complex of metal-aromatic compound.

20. The process of claim 19, wherein the first base agent and the second base agent are independently pyridine, triethylamine, 2,6-tert-butyl-pyridine, 2,6-tert-butyl-4-methyl-pyridine, N,N,N',N'-tetramethyl-naphthalene-1,8-diamine, N-1-Naphthylethylenediamine, sodium hydride, potassium hydride, or Naphthalene-•Li+.

21. The process of claim 15, further comprising the step of:
A') reacting 10-DAB with methyl sulfate to obtain the baccatin derivative (A) of claim 15,

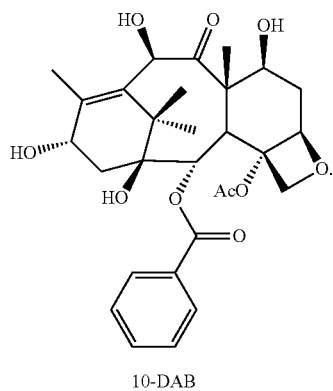

10-DAB

22. The process of claim 15, wherein the step A') is carried out in the presence of a base.

23. The process of claim 15, wherein the step A') is carried out in the presence of a Lewis acid.

* * * * *